US009317927B2

(12) United States Patent
Hamarneh et al.

(10) Patent No.: US 9,317,927 B2
(45) Date of Patent: Apr. 19, 2016

(54) METHODS AND SYSTEMS FOR INTERACTIVE 3D IMAGE SEGMENTATION

(71) Applicant: Oxipita Inc., Vancouver (CA)

(72) Inventors: Ghassan Hamarneh, Vancouver (CA); Rafeef Abugharbieh, Vancouver (CA); Andrew Top, San Francisco, CA (US)

(73) Assignee: Oxipita Inc., Vancouver, British Columbia ( * ) Notice: Subject to any disclaimer, the term of this patent is extended or adjusted under 35 U.S.C. 154(b) by 0 days.

(21) Appl. No.: 14/216,404

(22) Filed: Mar. 17, 2014

(65) Prior Publication Data

US 2014/0198979 A1 Jul. 17, 2014

Related U.S. Application Data

(63) Continuation of application No. PCT/CA2011/050571, filed on Sep. 19, 2011.

(51) Int. Cl.
*G06K 9/00* (2006.01)
*G06T 7/00* (2006.01)
(Continued)

(52) U.S. Cl.
CPC .............. *G06T 7/0097* (2013.01); *A61B 6/03* (2013.01); *G06T 7/0081* (2013.01); *A61B 6/467* (2013.01); *A61B 6/5211* (2013.01); *G06T 2207/10081* (2013.01); *G06T 2207/20092* (2013.01); *G06T 2207/30008* (2013.01)

(58) Field of Classification Search
CPC .............. G06T 7/0097; G06T 7/0081; G06T 2207/30008; G06T 2207/10081; G06T 2207/20092; A61B 6/03; A61B 6/467; A61B 6/5211

See application file for complete search history.

(56) References Cited

U.S. PATENT DOCUMENTS 6,606,091 B2 8/2003 Liang et al.
6,937,760 B2 8/2005 Schoepflin et al.
(Continued)

FOREIGN PATENT DOCUMENTS

WO 2011110960 A1 9/2011

OTHER PUBLICATIONS

M. Poon et al. "Efficient interactive 3D Livewire segmentation of complex objects with arbitrary topology", ScienceDirect, Computerized Medical Imaging and Graphics 32 (2008), 639-650.

(Continued)

*Primary Examiner* — Samir Ahmed
(74) *Attorney, Agent, or Firm* — Todd A. Rattray; Oyen Wiggs Green & Mutala LLP

(57) ABSTRACT

Methods and systems for interactively segmenting 3D image data are provided. An initial segmentation of the 3D image data is obtained, and for each of a plurality of image regions, a segmentation uncertainty indicator for the initial image segmentation is associated with the image region and a strength is assigned to the segmentation uncertainty indicator. A low-confidence region in the 3D image data is identified based at least in part on proximity of the low-confidence region to the image regions and strengths of the corresponding segmentation uncertainty indicators. An optimization routine may be applied to an objective function whose value depends at least in part on proximity of the candidate region to the image regions and the strengths of the corresponding uncertainty indicators to identify the low-confidence region from among a plurality of candidate regions.

40 Claims, 9 Drawing Sheets

(51) Int. Cl.
*A61B 6/03* (2006.01)
*A61B 6/00* (2006.01)

(56) References Cited

U.S. PATENT DOCUMENTS

| | | | |
|---|---|---|---|
| 7,561,725 | B2 | 7/2009 | Liang |
| 7,715,627 | B2 | 5/2010 | Sun et al. |
| 7,869,648 | B2 | 1/2011 | Schiller et al. |
| 7,876,934 | B2 | 1/2011 | Georgescu et al. |
| 8,050,498 | B2 | 11/2011 | Wilensky et al. |
| 8,897,544 | B2 * | 11/2014 | Christopher et al. ......... 382/154 |
| 2007/0297561 | A1 * | 12/2007 | Breeuwer et al. ................. 378/4 |
| 2008/0193006 | A1 | 8/2008 | Udupa et al. |
| 2009/0245625 | A1 | 10/2009 | Iwaki et al. |
| 2010/0232686 | A1 | 9/2010 | Dewan et al. |
| 2010/0322489 | A1 | 12/2010 | Tizhoosh et al. |
| 2011/0216965 | A1 | 9/2011 | Rother et al. |
| 2013/0121549 | A1 * | 5/2013 | Pekar et al. ................... 382/128 |

OTHER PUBLICATIONS

Lu K, Higgins W. Improved 3D live-wire method with application to 3D CT chest image analysis. SPIE Medical Imaging 2006:189-203.
Falcao A, Udupa J. A 3D generalization of user-steered live-wire segmentation. Medical Image Analysis 2000;4:389-402.
Praβni et al. "Uncertainty-Aware Guided Volume Segmentation", IEEE Vis conference, Nov.-Dec. 2010.
Saad et al. "ProbExplorer: Uncertainty-guided Exploration and Editing of Probabilistic Medical Image Segmentation", IEEE EuroVis in Jun. 2010.
Saad et al. "Exploration and Visualization of Segmentation Uncertainty Using Shape and Appearance Prior Information", IEEE Vis in Oct. 2010.
Rajapakse J, Kruggel F. Segmentation of MR images with intensity inhomogeneities.lmage and Vision Computing 1998;16:165-80.
Olabarriaga S, Smeulders A. Interaction in the segmentation of medical images: a survey. Medical Image Analysis 2001;5:127-42.
Kang Y, Engelke K, Kalender W. Interactive 3D editing tools for image segmentation. Medical Image Analysis 2004;8:35-46.
McInerney T, Terzopoulos D. Deformable models in medical image analysis: a survey. Medical Image Analysis 1996;1:91-108.
Kass M, Witkin A, Terzopoulos D. Snakes: active contour models. International Journal of Computer Vision 1988;1 (4):321-31.
McInerney T, Terzopoulos D. T-snakes: topology adaptive snakes. Medical Image Analysis 2000;4:73-91.
Delingette H. General object reconstruction based on simplex meshes. IJCV 1999;32:111-46.
Lachaud J-O, Montanvert A. Deformable meshes with automated topology changes for coarse-to-fine 3D surface extraction. Medical Image Analysis 1998;3(2):187-207.
Montagnat J, Delingette H, Ayache N. A review of deformable surfaces: topology, geometry and deformation. Image and Vision Computing 2001;19(14):1023-40.
Liang J, McInerney T, Terzopoulos D. United snakes. Medical Image Analysis 2006;10:215-33.
Lu, K, Higgins, W.E. Interactive segmentation based on the live wire for 3D CT chest image analysis, CARS 2007.
Caselles V, Kimmel R, Sapiro G. Geodesic active contours. IJCV 1997;22(1):61-79.
Ma, A., Patel, N., Li, M., Sethi, I.: Confidence based active learning for whole object image segmentation. In: Gunsel, B., Jain, A., Tekalp, A., Sankur, B. (eds.) Multimedia Content Representation, Classification and Security, vol. 4105, pp. 753-760. Springer Berlin / Heidelberg (2006).
Bresson X, Esedoglu S, Vandergheynst P, Thiran J-P, Osher S. Fast global minimization of the active contour/snake model. Journal of Mathematical Imaging and Vision 2007;28(2):151-67.
Cohen L, Kimmel R. Global minimum for active contour models: a minimal path approach. IJCV 1997;24:57-78.
Paragios N. User-aided Boundary Delineation through the Propagation of Implicit Representations MICCAI 2003:678-86.

Rumpf M, Strzodka R. Level set segmentation in graphics hardware. IEEE International Conference on Image Processing 2001:1103-6.
Lefohn A, Cates J, Whitaker R. Interactive GPU-Based Level Sets for 3D Segmentation MICCAI 2003:564-72.
Yushkevich P, Piven J, Hazlett H, Smith R, Ho S, Gee J, et al. User-guided 3D active contour segmentation of anatomical structures: significantly improved efficiency and reliability. NeuroImage 2006;31:1116-28.
McInerney T., Akhavan Sharif MR. Sketch Initialized Snakes for Rapid, Accurate and Repeatable Interactive Medical Image Segmentation ISBI 2006:398-401.
Urschler M, Mayer H, Bolter R, Leberl F. The livewire approach for the segmentation of left ventricle electron-beam CT images. In: 26th workshop of the Austrian association for pattern recognition (AGM/AAPR). 2002.
Gougoutas A, Wheaton A, Borthakur A, Shapiro E, Kneeland J, Udupa J, et al. Cartilage volume quantification via live wire segmentation. Academic Radiology 2004;11(Jan.):1389-95.
Zhang H, Nosher J, Yim P. Surface Reconstruction from Orthogonal Contours. SPIE Medical Imaging 2006:98-104.
Jackowski M, Satter M, Goshtasby A. Approximating digital 3D shapes by rational gaussian surfaces. IEEE Transactions on Visualization and Computer Graphics 2003;9(1):56-69.
Zhao H, Osher S, Merriman B, Kang M. Implicit, nonparametric shape reconstruction from unorganized points using a variational level set method. Computer Vision and Image Understanding 2000;80:295-319.
Turk G, O'Brien J. Shape transformation using variational implicit functions. In: Proceedings of the SIGGRAPH 99: Computer Graphics. 1999. p. 335-42.
Hoppe H, DeRose T, Duchamp T, McDonald J, StuetzleW. Surface reconstruction from unorganized points. In: SIGGRAPH '92: Proceedings of the 19th annual conference on computer graphics and interactive techniques. New York, NY, USA: ACM Press; 1992. p. 71-8.
Saboo R, Rosenman J, Pizer S. Geointerp: contour interpolation with geodesic snakes. The Insight Jounal 2006.
Boykov Y, Jolly M. Interactive Organ Segmentation Using Graph Cuts, MICCAI 2000:276-86.
Boykov Y, Funka-Lea G. Graph cuts and efficient N-D image segmentation. International Journal of Computer Vision 2006;70(2):109-31.
Rother C, Kolmogorov V, Blake A. GrabCut: interactive foreground extraction using iterated graph cuts. ACM Transactions on Graphics 2004:309-14.
Grady L. Random walks for image segmentation. IEEE Transactions Pattern Analysis and Machine Intelligence 2006; 28(11): 1768-83.
Barrett W, Mortensen E. Interactive live-wire boundary extraction. Medical Image Analysis 1997;1:331-41.
Chodorowski A, Mattsson U, Langille M, Hamarneh G. Color lesion boundary detection using live wire. SPIE Medical Imaging 2005:1589-96.
Falcao A, Udupa J, Samarasekera S, Sharma S, Hirsch B, Lotufo R. Usersteered image segmentation paradigms: live wire and live lane. Graphical Models and Image Processing 1998;60:233-60.
Falcao A, Udupa J, Miyazawa F. An ultra-fast user-steered image segmentation paradigm: live wire on the fly. IEEE TMI 2000; 19(Jan.):55-62.
Kang HW, Shin SY. Enhanced lane: interactive image segmentation by incremental path map construction. Graphical Models 2002;64(5):282-303.
Schenk A, Prause G, Peitgen H. Local cost computation for efficient segmentation of 3D objects with live wire. SPIE Medical Imaging 2001:1357-64.
Souza A, Udupa J, Grevera G, Sun DOY, Suri N. Iterative live wire and live snake: new user-steered 3D image segmentation paradigms. SPIE Medical Imaging 2006;(Mar.):1159-65.
Schenk A, Prause G, Peitgen H. Efficient semiautomatic segmentation of 3D objects in medical images. MICCAI 2000:186-95.
Falcao A, Bergo F. Interactive volume segmentation with differential image foresting transforms. IEEE TMI 2004;23:1100-8.
Settles, B.: Active learning literature survey. Tech. Rep. 1648, University of Wisconsin-Madison (2010).

(56) References Cited

OTHER PUBLICATIONS

Pavlopoulou, C., Kak, A.C., Brodley, C.: Applications of semi-supervised and active learning to interactive contour delineation. In: ICML 2003 Workshop on the Continuum from Labeled to Unlabeled Data in Machine Learning and Data Mining. pp. 26-33 (2003).

Mortensen, E.N., Barrett, W.A.: Intelligent scissors for image composition. In: 22nd annual conference on Computer graphics and interactive techniques. pp. 191-198. SIGGRAPH, ACM (1995).

Hamarneh G, Yang J, McIntosh C, Langille M. 3D live-wire-based semi-automatic segmentation of medical images. SPIE Medical Imaging 2005:1597-603.

Li, J., Bioucas-Dias, J., Plaza, A.: Supervised hyperspectral image segmentation using active learning. In: 2010 2nd Workshop on Hyperspectral Image and Signal Processing: Evolution in Remote Sensing. pp. 1-4 (2010).

Poon M, Hamarneh G, Abugharbieh R. Segmentation of complex objects with non-spherical topologies from volumetric medical images using 3D livewire. SPIE Medical Imaging 2007;6512-31:1-10.

Canny J. A computational approach to edge detection. IEEE Transactions Pattern Analysis and Machine Intelligence 1986;8(6):679-98.

Dijkstra E. A note on two problems in connexion with graphs. In Numerical Mathematik 1959;1:269-70.

Ackerman M. The visible human project. Proceedings of the IEEE 1998;86:504-11.

C. J. Armstrong, B. L. Price, and W. A. Barrett. Interactive segmentation of image vols. with live surface. Computers and Graphics, 31(2):212-229, 2007.

Grady, L, Schiwietz, T., Aharon, S., Westermann, R.: Random walks for interactive organ segmentation in two and three dimensions: Implementation and validation. In: Duncan, J., Gerig, G. (eds.) MICCAI. LNCS, vol. 3750, pp. 773-780. Springer Berlin / Heidelberg (2005).

T. Heimann et al. Comparison and evaluation of methods for liver segmentation from CT datasets. IEEE Transactions on Medical Imaging, 28(8):1251-1265, 2009.

L. Grady and G. Funka-Lea. An energy minimization approach to the data driven editing of presegmented images/volumes. In Medical Image Computing and Computer-Assisted Intervention, vol. 4191/2006, pp. 888-895, 2006.

L. Grady and A. K. Sinop. Fast approximate random walker segmentation using eigenvector precomputation. In IEEE Computer Vision and Pattern Recognition, pp. 1-8, 2008.

P. Kohli and P. H.S. Torr. Measuring uncertainty in graph cut solutions—efficiently computing min-marginal energies using dynamic graph cuts. In ECCV Computer Vision, pp. 30-43, 2006.

F. Malmberg, E. Vidholm, and Nystrom. A 3D live-wire segmentation method for volume images using haptic interaction. In Discrete Geometry for Computer Imagery, vol. 4245/2006, pp. 663-673, 2006.

J. Y. Yen. Finding the K shortest loopless paths in a network. Management Science, 17:712-716, 1971.

Chan, T., Vese, L.: Active contours without edges. IEEE Trans. Image Proc. 10(2), 266-277 (2001).

\* cited by examiner

METHODS AND SYSTEMS FOR INTERACTIVE 3D IMAGE SEGMENTATION

RELATED APPLICATIONS

This application is a continuation of PCT application No. PCT/CA2011/050571 having an international filing date of 19 Sep. 2011 which is hereby incorporated herein by reference.

TECHNICAL FIELD

The application relates to segmentation of three-dimensional (3D) images. Some embodiments provide methods and apparatus for guiding user intervention in semi-automatic image segmentation methods.

BACKGROUND 3D image segmentation is an important and ubiquitous task in many fields. Image segmentation is the process of dividing an image into a plurality segments which correspond to different characteristics. For example, a computed tomography image of a femur may be segmented into bone and background segments. Non-limiting uses of image segmentation include:
- simplifying and/or enhancing images;
- identifying and/or highlighting objects in images;
- creating representations of objects depicted in images (e.g., 3D model reconstructions).

Image segmentation can be represented in various ways, such as by description of segment boundaries (e.g., by curves, surfaces, and the like), and values assigned to image regions (e.g., values assigned to pixels, voxels or other coordinates corresponding to image locations). Values assigned to image regions may comprise labels (e.g., indicating that the labelled image region has, or has been determined to have, a particular characteristic), or probabilities (e.g., indicating the probability that the corresponding region has a particular characteristic). For example, an image segmentation may assign every voxel in a 3D image a label having a value of 0 or 1 to indicate that the voxel belongs to the background or a foreground object, or may assign every voxel in a 3D image a probability value in the range of 0 to 1 to indicate that probability that the voxel belongs to a particular object. In some cases, there may be multiple objects (e.g. multiple types of tissues) within a given 3D image and an image segmentation may assign multiple probabilities to each voxel in the image, with each probability representing a likelihood that the voxel corresponds to a particular one of the multiple objects.

A wide variety of 3D image segmentation techniques is known. Image segmentation techniques can be characterized by the degree of user interaction they require. At one extreme, image segmentation may be a completely manual process, in which all segmentation decisions are made by a user. An example of completely manual 3D image segmentation is manual slice-by-slice segmentation, in which a 3D image is divided into component image planes, and each plane segmented by a human operator. Manual slice-by-slice segmentation is widely recognized as impractical, being too tedious, time consuming, expensive, and suffering from high inter- and intra-operator variability.

At the other extreme, image segmentation may be a completely automatic process, in which all segmentation decisions are made by a machine (e.g., a programmed computer). Known fully-automated segmentation techniques generally lack the accuracy and robustness required for segmenting images having variable structure(s) and/or for segmentation applications where accuracy is paramount (e.g., medical images depicting anatomical structures affected by subject diversity and/or pathology). Fully-automated segmentation techniques are typically only suitable for images with common or predictable structure(s) and generally require careful tuning according to image properties to operate acceptably.

In between these extremes lie semi-automated segmentation techniques, which combine user input with automated segmentation decision making. Some semi-automated segmentation techniques are iterative. Iterative semi-automated segmentation techniques typically involve iteratively repeating the blocks of: providing user input; and automatically generating a segmentation based on the user input. User input to iterative semi-automated segmentation techniques may be based on a previous segmentation together with available image data and may be intended to yield a subsequent segmentation that is improved over the previous segmentation. In one exemplary semi-automated segmentation process, an initial iteration involves: obtaining user input based on the image data; and generating an initial segmentation based on the user input and the image data. Second and subsequent iterations may then involve: obtaining further user input based on the image data together with the previous segmentation; and generating a segmentation based on the user input, the image data and the previous segmentation. In other embodiments, semi-automated segmentation processes may involve automatically generating a segmentation in a first iteration and then obtaining user input for second and subsequent iterations. Semi-automated segmentation techniques may also be referred to as interactive segmentation techniques.

FIG. 1 is a schematic diagram of an exemplary interactive segmentation technique 10 for segmenting 3D image data 14. An image segmentation 12 and a portion (e.g. a slice) of 3D image data 14 may be displayed to an operator O on a display 16. Operator O provides user input 18 at user interface 20. User input 18, which may be based on 3D image data 14 and/or a previous segmentation 12, is provided to a segmentation engine 22. Segmentation engine 22 automatically generates a new segmentation 12 which may be based on user input 18, 3D image data 14 and a previous segmentation 12. The process of providing user input 18 based on image segmentation 12 and then generating a revised segmentation 12 constitutes a loop 24. Loop 24 may be repeated, with user data 18 provided in each iteration accumulating in segmentation engine 22, such that the revised segmentations 12 produced in successive iterations of loop 24 are based on increasing amounts of user input 18. To the extent that user input 18 is reliable, segmentation 12 can be expected to improve with successive iterations of loop 24.

A problem with interactive segmentation techniques is that it may not be clear to a human operator what particular user input would most improve the segmentation. Though an understanding of the algorithm used to automatically generate a segmentation may provide some sense of what sort of input would more likely improve a segmentation, such understanding may be uncommon among those who perform segmentation. For example, doctors and clinicians involved in performing segmentation of medical images may not appreciate the intricacies involved in 3D segmentation algorithms. Even those with such an understanding may fail to provide optimal or near optimal input due to the complexity of the algorithm, difficulty perceiving features of a segmentation, and the like. Accordingly there is need for methods and apparatus that improve the quality of user input provided to interactive 3D image segmentation techniques.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

An aspect of the invention provides a method for segmenting 3D image data, the method including obtaining an initial segmentation of the 3D image data, and for each of a plurality of image regions, associating a segmentation uncertainty indicator for the initial image segmentation with the image region and assigning a strength to the segmentation uncertainty indicator. A low-confidence region in the 3D image data may be identified based at least in part on proximity of the low-confidence region to the image regions and strengths of the corresponding segmentation uncertainty indicators. In some embodiments, identifying the low-confidence region in the 3D image data comprises computing, for each of a plurality of candidate regions, a value of an objective function based at least in part on proximity of the candidate region to the image regions and the strengths of the corresponding uncertainty indicators. The value of the objective function for a candidate region may be based on the proximity of the candidate region to each of the image regions scaled according to the strength of the corresponding uncertainty indicator.

Another aspect of the invention provides a system for segmenting 3D image data. The system includes a controller having an uncertainty indicator generator and a low-confidence region identifier, a display operatively coupled to the controller, and a user interface operatively coupled to the controller. The controller is configured to obtain an initial segmentation of the 3D image data. The uncertainty indicator generator is configured to, for each of a plurality of image regions, associate a segmentation uncertainty indicator for the initial image segmentation with the image region and assign a strength to the segmentation uncertainty indicator. The low-confidence region identifier is configured to identify a low-confidence region in the 3D image data based at least in part on proximity of the low-confidence region to the image regions and strengths of the corresponding segmentation uncertainty indicators. The controller may be configured to cause the display to display an indication of the low-confidence region, to obtain an image segmentation for the low-confidence region based on user input entered at the user interface.

Another aspect of the invention provides a method for recommending an image region for which further user input would be desirable in an interactive 3D segmentation process, the method comprising: obtaining 3D image data and a first segmentation of the 3D image data; for each of a plurality of image regions, associating an uncertainty indicator for the initial image segmentation with the image region and assigning a strength to the uncertainty indicator; identifying a low-confidence region in the 3D image data based at least in part on proximity of the low-confidence region to the image regions and strengths of the corresponding uncertainty indicators; and recommending the low-confidence region to be the image region for which further user input would be desirable.

Other aspects of the invention comprises computer program products for segmenting 3D image data, the program product comprising a non-transitory computer-readable medium having executable code configured to cause a processor executing the code to perform the methods described herein.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

In drawings which illustrate non-limiting embodiments.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
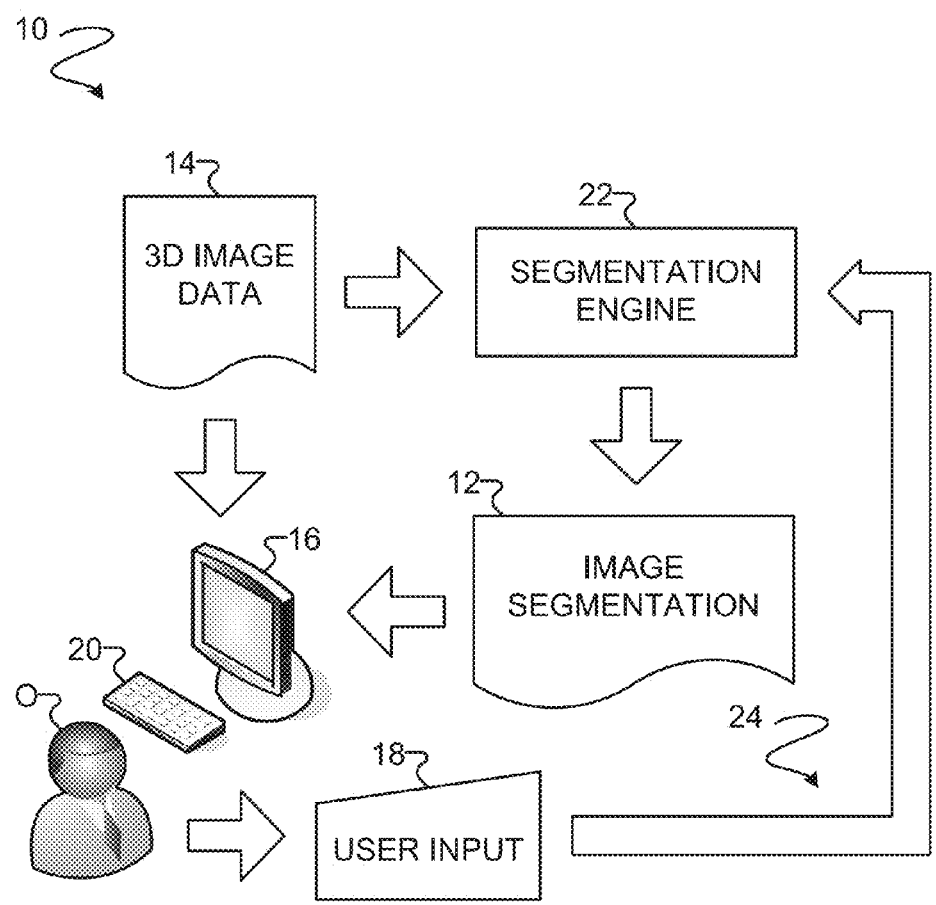
FIG. 1 schematically illustrates a 3D interactive segmentation process.
Figure 2:
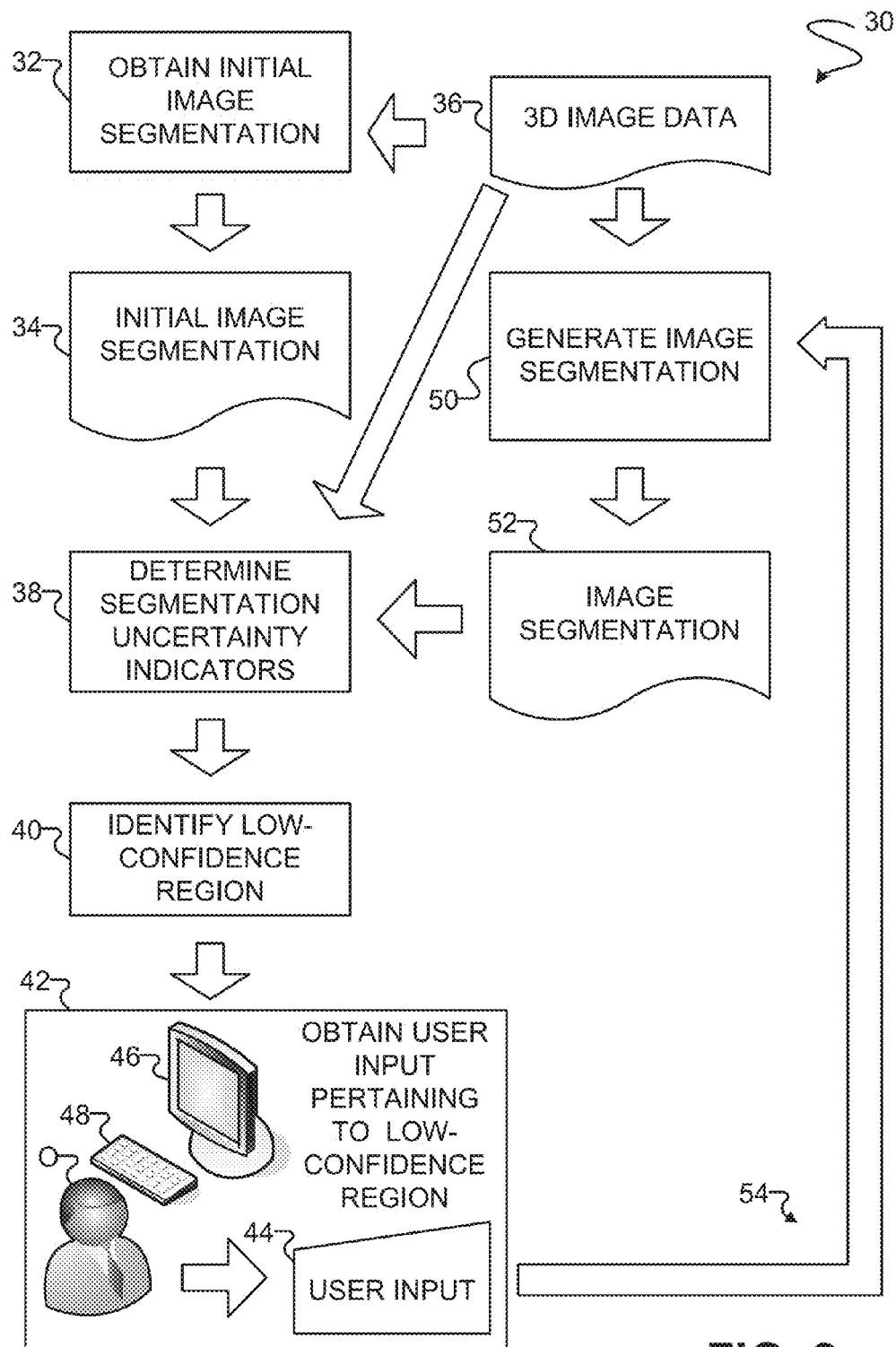
FIG. 2 is a flowchart showing a method for 3D image segmentation according to an example embodiment.

FIG. 2 is a flowchart of a method 30 for segmentation of 3D image data 36 according to an example embodiment. Image data 36 may generally comprise any 3D image data. Image data 36 may be generated using a Computed Tomography (CT) scan, a Magnetic Resonance Imaging (MRI) scan, a Positron Emission Tomography scan, and/or the like. Image data 36 may comprise any suitable format of image representation, including by way of non-limiting example: monochromatic luminosity or intensity (also referred to in some fields as the Y channel), one or more color channels (e.g. R, G, B) and/or the like.

Method 30 begins in block 32, which involves obtaining an initial image segmentation 34 for 3D image data 36. Image segmentation 34 may be obtained in block 32 using any suitable technique. Block 32 may comprise generating image segmentation 34 automatically, semi-automatically or manually. In some embodiments, block 32 comprises obtaining image segmentation 34 from an external source.

Method 30 then proceeds to block 38, which involves associating one or more segmentation uncertainty indicators for image segmentation 34 with corresponding image region(s) in 3D image data 36, and assigning a strength to each of the one or more uncertainty indicators. The strength of a segmentation uncertainty indicator reflects uncertainty (e.g. a lack of confidence) that segmentation 34 correctly characterizes a corresponding image region of 3D image data 36. Relatively low and high strengths of an uncertainty indicator may be respectively indicative of relatively high and low levels of confidence in the current segmentation in the image region corresponding to the uncertainty indicator.

Segmentation uncertainty indicators may be determined based at least in part on one or any combination of image segmentation 34, image data 36, and trusted segmentation information (e.g., segmentation information provided or approved by a user, including image segmentation information used to generate image segmentation 34). For instance, uncertainty indicators may be determined in block 38 based on:
- conformance of image segmentation 34 to 3D image data 36 (e.g., image gradient similarity between a region of image data 36 that image segmentation 34 indicates corresponds to a particular anatomical structure and a reference image of the anatomical structure, image intensity similarity between a region of image data 36 that image segmentation 34 indicates corresponds to a particular segment and an image intensity distribution for the image feature(s) denoted by the segment, etc.);
- conformance of image segmentation 34 to another image segmentation for 3D image data 36;
- the quality (e.g., resolution, contrast, edge strength, noise, image artefacts, partial volume effects, intensity heterogeneity etc.) of image data 36;
- conformance of image segmentation 34 to one or more expected image segmentation properties (e.g., 3D shape similarity of image segmentation 34 to a reference shape, 2D similarity of a cross-section of image segmentation 34 to a reference cross-section, surface geometry similarity of image segmentation 34 (or a portion thereof) to a reference surface geometry (such as smoothness, for example), etc.);
- a model of the efficacy of trusted segmentation information from which the segmentation was determined;
- any combination of the above; and/or
- the like.

Particular non-limiting examples of uncertainty indicators and methods for determining uncertainty indicators are described below.

The strength of block 38 segmentation uncertainty indicators may be expressed in scalar and/or vector values. The block 38 uncertainty indicators may have binary values (e.g. 0 or 1) or may have a range of possible values (e.g. in a normalized range [0,1]). The block 38 determination of segmentation uncertainty indicators may, in some embodiments, depend on the method used to generate segmentation 34.

Each of the block 38 uncertainty indicators is associated with a corresponding image region. Image regions for which the block 38 uncertainty indicators are determined may be defined in some coordinate system that spans the space of image data 36. Such a coordinate system may have an accuracy that is finer than the size of voxels in image data 36. The image regions corresponding to the block 38 uncertainty indicators may generally comprise any regions in such a coordinate system. In one particular example, the image regions corresponding to the block 38 uncertainty indicators may be defined to comprise one or more voxels or groups of voxels in image data 36, although this is not necessary.

Block 38 may comprise determining a plurality of different uncertainty indicators for the same image region. In some embodiments, each of a plurality of different uncertainty indicators corresponding to a particular image region may be determined based on a different set of criteria. In some embodiments, block 38 comprises determining uncertainty indicators for a set of image regions whose union spans the space of image data 36. For example, block 38 may comprise determining an uncertainty indicator for every voxel of image data 36. In other embodiments, block 38 comprises determining uncertainty indicators for a set of image regions whose union corresponds to a subset of the space of image data 36.

Method 30 then proceeds to block 40 which involves using the block 38 uncertainty indicators to identify a low-confidence region of the current image segmentation (e.g. initial segmentation 34 for the first iteration of block 40 and segmentation 52 for the second and subsequent iterations). Block 40 may comprise identifying a low-confidence region in the 3D image data 36 based at least in part on proximity of the low-confidence region to the image regions corresponding to segmentation uncertainty indicators determined in block 38 and the strengths of these segmentation uncertainty indicators.

In some embodiments, block 40 comprises identifying a low-confidence region from among a plurality of candidate regions. For example, block 40 may involve identifying a low-confidence region by performing an optimization routine which maximizes (or minimizes) an objective function (known variously in the art of optimization as a cost function, energy function, etc.) across the set of candidate regions. Those skilled in the art will appreciate that there are a wide variety of known optimization routines and that any suitable one or more of these optimization routines may be used in block 40. In some embodiments, multiple optimizations may be performed using different initial conditions and the block 40 low-confidence region may be selected from among the output regions of these optimizations—i.e. to avoid issues with local extrema during optimization.

The objective function used for the identification of a low-confidence region in block 40 may assign a value to a particular candidate region based on properties of the block 38 uncertainty indicators and properties of the particular candidate region. In some embodiments, the objective function may assign a value to a particular candidate region based on a strength of the block 38 uncertainty indicators and a proximity metric relating a position of the image region for each block 38 uncertainty indicator to a position of the candidate region. In some particular embodiments, the objective function may assign a value to a particular candidate region based on (e.g., proportional to) a strength of the block 38 uncertainty indicators scaled according to a proximity of their corresponding image regions from the candidate region. For example, block 40 may involve evaluating candidate regions using an objective function:

$$E(R) = \Sigma_{i \in UI} s_i L(p_i, R) \tag{1}$$

where: R represents a position of the candidate region; UI is the set of block 38 uncertainty indicators indexed by the index variable i; $S_i$ is the strength of the $i^{th}$ uncertainty indicator; $p_i$ is the position of the image region corresponding to the $i^{th}$ uncertainty indicator; and L is a proximity metric function whose value monotonically decreases with separation between R and $p_i$. It will be appreciated that R and $p_i$ may be vector quantities. The block 40 low-confidence region may be identified as the candidate region corresponding to the maximum value of the equation (1) objective function.

In some embodiments, block 40 may involve identifying a plurality of low-confidence regions. Such a plurality of low-confidence regions may be ranked in some way to identify those of lowest confidence (e.g. highest uncertainty). In some embodiments, identifying a plurality of low-confidence regions may involve: (i) performing a first optimization routine which maximizes (or minimizes) an objective function across a set of candidate regions to identify a first low-confidence region; (ii) re-assigning low strengths (e.g. artificially low strengths) to the uncertainty indicators in a vicinity of the previously identified low-confidence region; (iii) performing a subsequent optimization routine with the re-assigned uncertainty indicator strengths to identify a subsequent low-confidence region; and (iv) repeating steps (ii) and (iii) until a desired number of low-confidence regions have been identified. The region of re-assignment of artificially low strength uncertainty indicators in a vicinity of a previously selected low-confidence region may be based on one or more user-configurable parameters. This artificial assignment of low strengths to uncertainty indicators may avoid outputting a plurality of low-confidence regions that are undesirably close to one another.

Particular non-limiting example methods for identifying low-confidence regions are described below.

At the conclusion of block 40, method 30 proceeds to block 42 which involves obtaining user input 44 for the block 40 low-confidence region. User input 44 obtained in block 42 may comprise user segmentation input 44. In some embodiments, block 42 may comprise displaying, on display 46, image data 36 (or a portion thereof) corresponding to the block 40 low-confidence region and obtaining, from operator O, a segmentation of the displayed image data input via user interface 48. User input 44 obtained in block 42 may be any input suitable for guiding any image segmentation technique. In some embodiments, the low-confidence region identified in block 40 comprises a 2D region (e.g., a planar surface), and block 42 comprises obtaining user segmentation input 44 that constructs a 2D image segmentation on the 2D low-confidence region according to a 2D image segmentation technique. In embodiments, where block 40 identifies more than one low-confidence region, block 42 may involve obtaining user segmentation input 44 for more than one low-confidence region. In some embodiments, the user segmentation input 44 obtained in block 42 may comprise semi-automatically generated segmentation information (e.g. a semi-automatically generated 2D segmentation).

After obtaining user input 44 in block 42, method 30 proceeds to block 50 which involves generating an image segmentation 52 of 3D image data 36 based at least in part on user segmentation input 44 obtained in block 42. In addition to being based on 3D image data 36 and user segmentation input 44, the block 50 image segmentation process may also be based on information from one or more previous segmentations of image data 36. The block 50 image segmentation process may comprise any suitable 3D image segmentation algorithm, including known and future image segmentation algorithms. Non-limiting examples of 3D image segmentation algorithms that may be used in block 50 include:

Turtle Map 3D Livewire, as described, for example, in M. Poon, G. Hamarneh, and R. Abugharbieh. Efficient interactive 3D livewire segmentation of complex objects with arbitrary topology. *Computerized Medical Imaging and Graphics,* 32:639-650, 2008;

Random Walker, as described, for example, in L. Grady. Random walks for image segmentation. *IEEE Trans. Pat. Anal. And Mach. Intel.* 28(11), 1768-1783, 2006.

Live Surface, as described, for example, in C. J. Armstrong, B. L. Price, and W. A. Barrett. Interactive segmentation of image volumes with live surface. *Computers and Graphics,* 31(2):212-229, 2007.

Graph cuts, as described, for example, in Y. Boykov and G. Funka-Lea. Graph cuts and efficient N-D image segmentation. *Medical Image Analysis,* 1:331-341, 1997.

Methods based on level sets as described, for example, in:
Aaron E. Lefohn, Joshua E. Cates and Ross T. Whitaker, Interactive, GPU-Based Level Sets for 3D Segmentation. *MICCAI,* Volume 2878, 564-572, 2003

Ho, S.; Bullitt, E.; Gerig, G, Level-set evolution with region competition: automatic 3-D segmentation of brain tumors. *ICPR,* 532-535 vol. 1, 2002.

Methods based on deformable meshes and surfaces, e.g.
J. Y. Park, T. McInerney, D. Terzopoulos, M. H. Kim, A Non-Self-Intersecting Deformable Surface for Complex Boundary Extraction from Volumetric Images. *Computers and Graphics,* 25(3), June, 2001, pages 421-440. Computers and Graphics 2001.

T. McInerney, D. Terzopoulos, A dynamic finite element surface model for segmentation and tracking in multidimensional medical images with application to cardiac 4D image analysis. *Computerized Medical Imaging and Graphics,* 19(1), January, 1995, pages 69-83. Special Issue on Cardiopulmonary Imaging.

M. Hébert, H. Delingette, and K. Ikeuchi. Shape Representation and Image Segmentation Using Deformable Surfaces. *IEEE Transactions on Pattern Analysis and Machine Intelligence,* 17(7), June 1995.

Camille Couprie, Leo Grady, Laurent Najman, Hugues Talbot, Power Watershed: A Unifying Graph-Based Optimization Framework, *IEEE PAMI,* July 2011 (vol. 33 no. 7), pp. 1384-1399.

Leo Grady, "Minimal Surfaces Extend Shortest Path Segmentation Methods to 3D", *IEEE Trans. on Pattern Analysis and Machine Intelligence,* Vol. 32, No. 2, pp. 321-334, February 2010, Registration/atlas/template based segmentation, as described, for example, in:
Gee J C, Reivich M., Bajcsy R (1993). Elastically Deforming an Atlas to Match Anatomical Brain Images, *J. Comp. Assist. Tomogr.* 17(2):225-236, March 1993.

D L Collins, C J Holmes, T M Peters, A C Evans, Automatic 3-D model-based neuroanatomical segmentation, *Human Brain Mapping,* 1995, Vol 3(3), 190-208.

D. Louis Collins, Alan C. Evans: Animal: Validation and Applications of Nonlinear Registration-Based Segmentation. *IJPRAI* 11(8): 1271-1294 (1997)

Iosifescu D V, Shenton M E, Warfield S K, Kikinis R, Dengler J, Jolesz F A, McCarley R W., An automated registration algorithm for measuring MRI subcortical brain structures, *Neuroimage,* 2997, vol. 6(1), 13-25.

T. F. Cootes, G. J. Edwards, and C. J. Taylor. Active appearance models. *IEEE TPAMI,* 23(6):681-685, 2001.

and/or the like.

The references listed in this paragraph are hereby incorporated herein by reference.

It will be appreciated that the method by which segmentation uncertainty indicators are determined in block 38 and/or the method by which low-confidence regions are identified in block 40 may be adapted so that the user segmentation input 44 obtained in block 42 results in an optimal or near-optimal improvement in image segmentation 52 when image segmentation 52 is generated in block 50. For example, as discussed above, block 40 may involve maximizing (or minimizing) an objective function (e.g. the objective function of equation (1)) which depends on candidate regions (for user input) and the block 38 uncertainty indicators, so as to identify an optimal block 40 low-confidence region from among the candidate regions and may then recommend to operator O that the block 42 user segmentation input 44 be directed at this optimal block 40 low-confidence region.

At the conclusion of block 50, an inquiry (not explicitly shown) may optionally be conducted to determine if the newly generated image segmentation 52 is acceptable. This inquiry may involve displaying the newly generated image segmentation 52 on display 46 and allowing operator O to visually inspect image segmentation 52 and to indicate the acceptability of the newly generated image segmentation 52 using user interface 48. If the newly generated image segmentation 52 is acceptable, then method 30 may be concluded.

If the block 50 inquiry determines that the newly generated image segmentation 52 is not acceptable, then method 30 proceeds to block 38 which involves determining uncertainty indicators. In the second and subsequent iterations of block 38, the block 38 uncertainty indicators are determined in relation to newly generated image segmentation 52 (as opposed to initial image segmentation 34 as described above). The image regions used to determine the block 38 uncertainty indicators for new image segmentation 52 may be the same or different from the image regions used to determine the block 38 uncertainty indicators for initial image segmentation 34.

As is apparent from the return to block 38, method 30 includes loop 54, which in the illustrated embodiment comprises blocks 38, 40, 42 and 50. Loop 54 may be repeated, with user data 44 accumulated in each iteration, such that in successive iterations of loop 54, block 50 generates image segmentation 52 using increasing amounts of user input 44. In some embodiments, block 40 may comprise comparing a value of an objective function for the block 40 identified low-confidence region to a threshold, and terminating method 30 if the objective function value indicates at least a threshold confidence in image segmentation 34, 52 input to block 38 (e.g. if the block 40 objective function for the identified low-confidence region is less than a threshold value, which may be user-configurable).

Figure 2A:
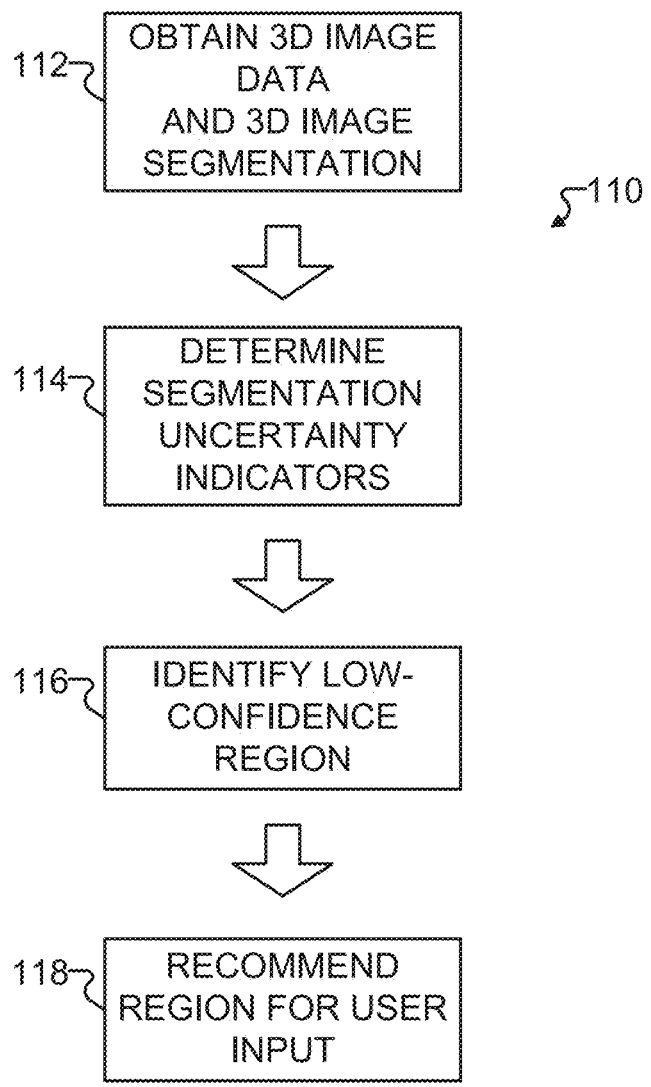
FIG. 2A is a flowchart showing a method for recommending optima user input for a 3D image segmentation according to an example embodiment.

FIG. 2A is a flowchart showing a method 110 for recommending a region (e.g. an optimal image region) for user input in a 3D image segmentation process according to an example embodiment. Method 110 comprises a number of processes which are similar to those of 3D segmentation method 30 described above. Method 110 begins in block 112 which involves obtaining 3D image data and a corresponding 3D image segmentation. The block 112 3D image segmentation may be obtained as a part of a 3D segmentation process in which method 110 forms a part. The block 112 image segmentation may be obtained using any suitable technique, including generating the block 112 image segmentation automatically, semi-automatically or manually. In some embodiments, block 112 comprises obtaining a 3D image segmentation from an external source.

Method 110 then proceeds to block 114 which involves determining uncertainty indicators for the block 112 3D segmentation. Obtaining uncertainty indicators in block 114 may be substantially similar to obtaining uncertainty indicators in block 38 described above and may be based on the block 112 3D segmentation and the block 112 3D image data. Method 110 then proceeds to block 116 which involves identifying one or more low-confidence regions for the block 112 3D segmentation. Identifying low-confidence region(s) in block 116 may be substantially similar to identifying low-confidence region(s) in block 40 discussed above and may be based on an optimization routine involving maximizing (or minimizing) an objective function over a set of candidate regions.

Method 110 then proceeds to block 118 which involves recommending one or more of the block 116 low-confidence region(s) to be an optimal region for receiving user segmentation input.

Figure 3:
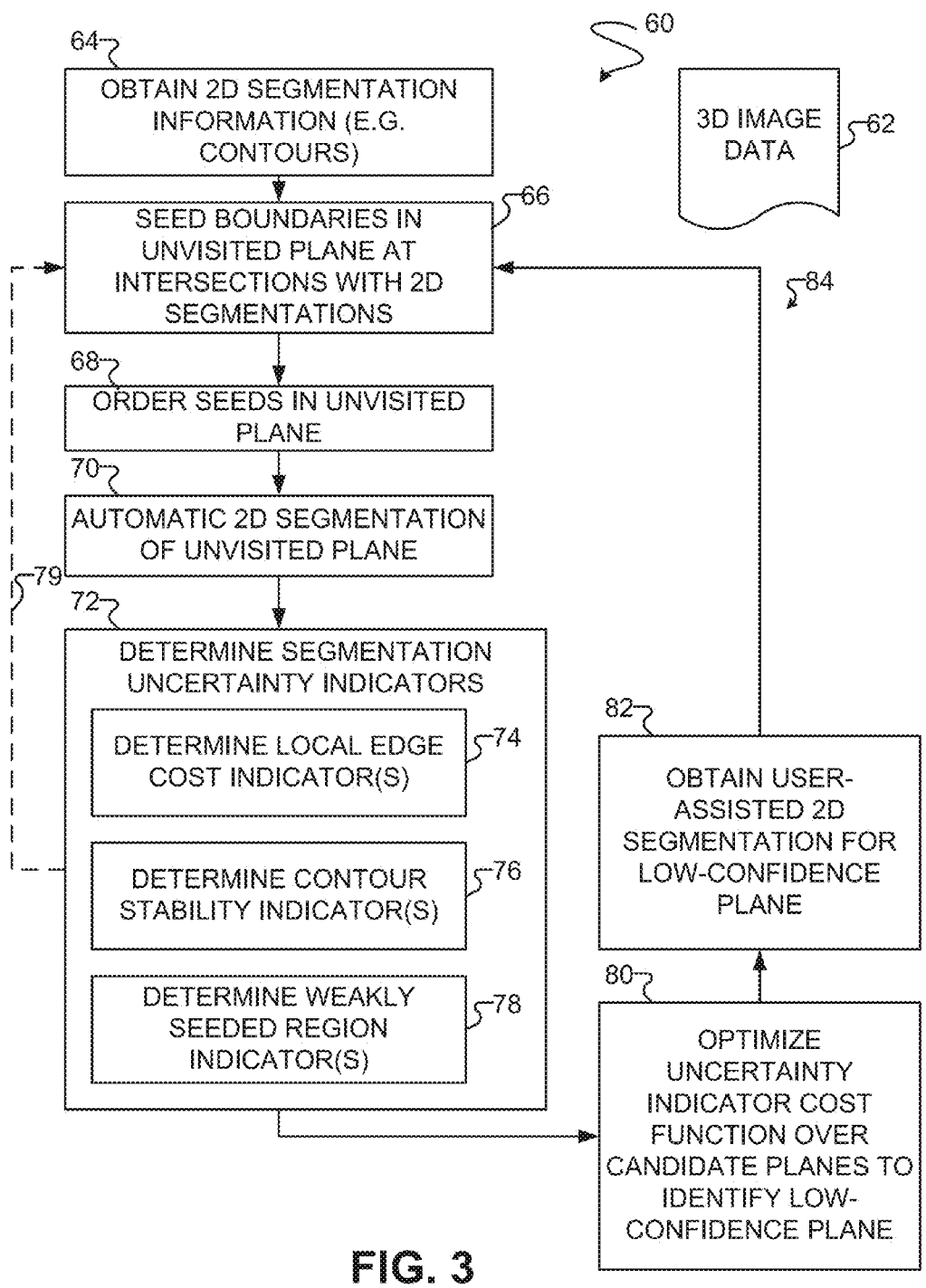
FIG. 3 is a flowchart showing a method for 3D image segmentation according to another example embodiment.

FIG. 3 is a flowchart of a method for 3D segmentation of 3D image data 62 according to another example embodiment. Method 60 illustrates a non-limiting example implementation of method 30.

Method 60 begins in block 64 which involves obtaining 2D segmentation information in respect of 3D image data 62. The block 64 2D segmentation information may be obtained via a manual, semi-automatic and/or automatic 2D segmentation process. The block 64 2D segmentation information may be provided in respect of one or more 2D surfaces (e.g. planes) of image data 62. In some cases, it may be preferable that the block 64 2D segmentation information be provided for two or more non-parallel planar slices of 3D image data 62. In some cases, it may be preferable that the block 64 2D segmentation information be provided for two or more intersecting planar slices of 3D image data 62. In some cases, such intersecting planar slices may be selected to be orthogonal slices, although this is not necessary.

In particular embodiments, the block 64 2D segmentation information comprises one or more 2D segmentation contours for one or more 2D (e.g. planar) slices of 3D image data 62, although this is not necessary. In other embodiments, the block 64 2D segmentation information need not comprise contours and may additionally or alternatively comprise: labels assigned to some or all pixels of one or more 2D (e.g. planar) image slices, which label the pixels as belonging to one of a set of image segments; probabilities assigned to some or all pixels of one or more 2D (e.g. planar) image slices, which indicate the probability of the pixels as belonging to one (or others) of a set of image segments; and/or the like.

For the remainder of the description of method 60, unless otherwise stated, it is assumed for ease of description and without loss of generality, that the block 64 2D segmentation information comprises one or more 2D segmentation contours for one or more 2D (e.g. planar) slices of 3D image data 62. As discussed above, the block 64 2D segmentation contours may be provided for a plurality of 2D (e.g. planar) slices of 3D image data 62, which may comprise two or more non-parallel planar slices of 3D image data 62, two or more intersecting (e.g., in the space of 3D image data 62) planar slices of 3D image data 62 and/or two or more orthogonal planar slices of 3D image data 62, although this is not necessary. Block 64 may comprise semi-automatically generating 2D segmentation contours using an interactive 2D segmentation technique, such as, the 2D Livewire algorithm, for example—see W. A. Barrett and E. N. Mortensen. Interactive livewire boundary extraction. *Medical Image Analysis*, 1:331-341, 1997, which is hereby incorporated herein by reference.

Figure 4A:
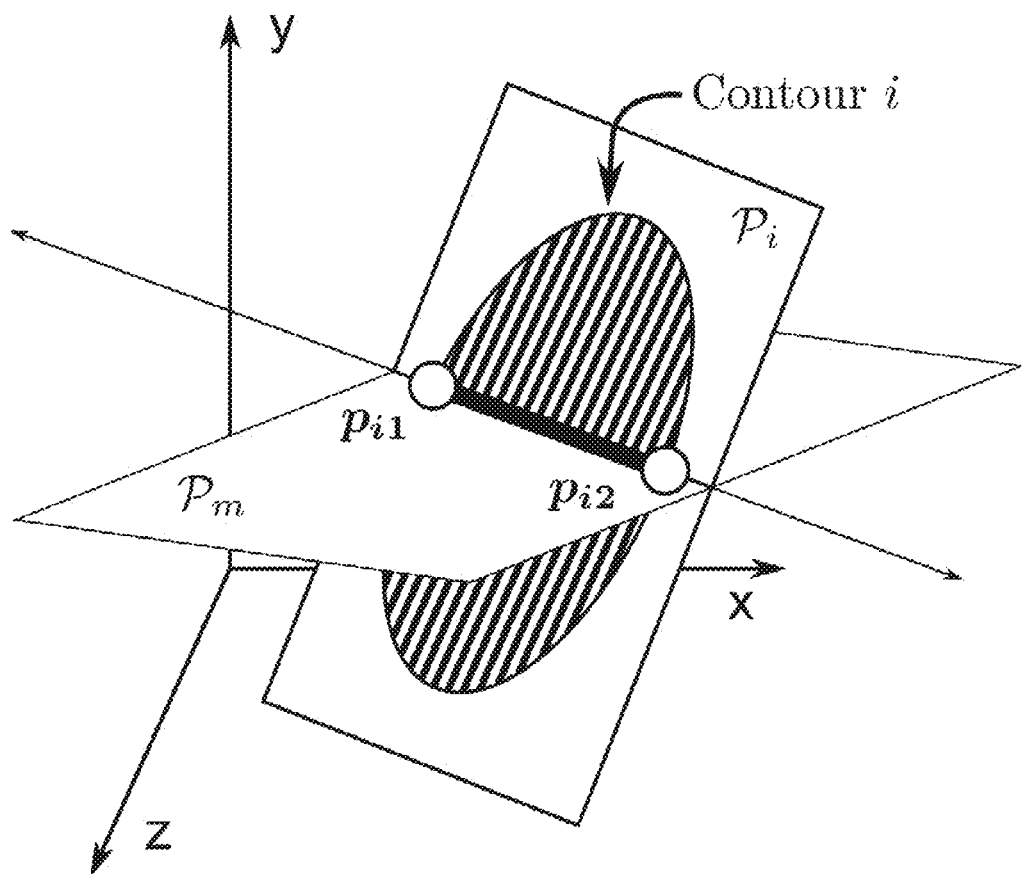
FIG. 4A is a schematic illustration showing how an unvisited plane may be seeded with seedpoints according to a particular embodiment.

Block 66 involves seeding (e.g. determining seedpoints on) boundaries of a 2D segmentation (e.g. a contour) for an arbitrary plane $P_m$ through image data 62. The arbitrary block 66 plane $P_m$ may be referred to as an "unvisited" plane, because $P_m$ may be selected to be a plane that was not involved (i.e. not "visited) while obtaining the block 64 2D segmentation information. The block 66 unvisited plane $P_m$ is preferably intersected by the 2D planar slices and corresponding 2D segmentation contours obtained in block 64. The block 66 boundary seeding process is shown schematically in FIG. 4A. In FIG. 4A, plane $P_i$ represents a plane on which a block 64 2D segmentation (contour i) is obtained. In the FIG. 4A embodiment, block 66 involves automatically determining seedpoints $p_{i1}$ and $p_{i2}$ to be located at the points where the block 64 2D segmentation (contour i) intersects the unvisited plane $P_m$. It will be appreciated that FIG. 4A shows the block 66 seeding in the unvisited plane $P_m$ for a single block 64 2D segmentation (contour i), but that additional seedpoints may be seeded (as part of block 66) on the unvisited plane $P_m$ for the intersection of other block 64 2D contours (not shown) with the unvisited plane $P_m$. The block 66 seedpoints (e.g. seedpoints $p_{i1}$ and $p_{i2}$ of FIG. 4A) may be assumed to be points on the boundary of a resultant 3D segmentation involving the unvisited plane $P_m$.

To the extent that the block 64 2D segmentation information comprises segmentation information (e.g. labels, probabilities and/or the like) that is different from contours, block 66 may involve making use of this segmentation information to determine seedpoints on the boundaries for the unvisited plane $P_m$. While this process may not be as graphically intuitive for other types of block 64 2D segmentation information, those skilled in the art will appreciated that this block 66 seeding process involves attempting to ascertain where label edges of the block 64 2D segmentation information intersect the unvisited plane $P_m$ and determining block 66 seedpoints to be at such intersections.

Block 68 involves ordering the block 66 seedpoints seeded on the unvisited plane $P_m$. In some embodiments, block 68 may comprise ordering the block 66 seedpoints by: defining line segments produced by connecting block 66 intersection points of each block 64 2D contour with the unvisited plane $P_m$ (e.g. the line segment connecting seedpoints $p_{i1}$ and $p_{i2}$ in FIG. 4A); forming a graph whose vertices are the line segment end points (e.g. the block 66 seedpoints) and the intersections between line segments; and ordering the block 66 seedpoints (e.g. the end points of the line segments) by choosing an arbitrary line segment end point to be an initial vertex and traversing the edges of the graph. The graph may be traversed by traversing an edge that forms the smallest oriented angle (e.g. counter-clockwise angle) with a previously traversed edge, for example.

Figure 4B:
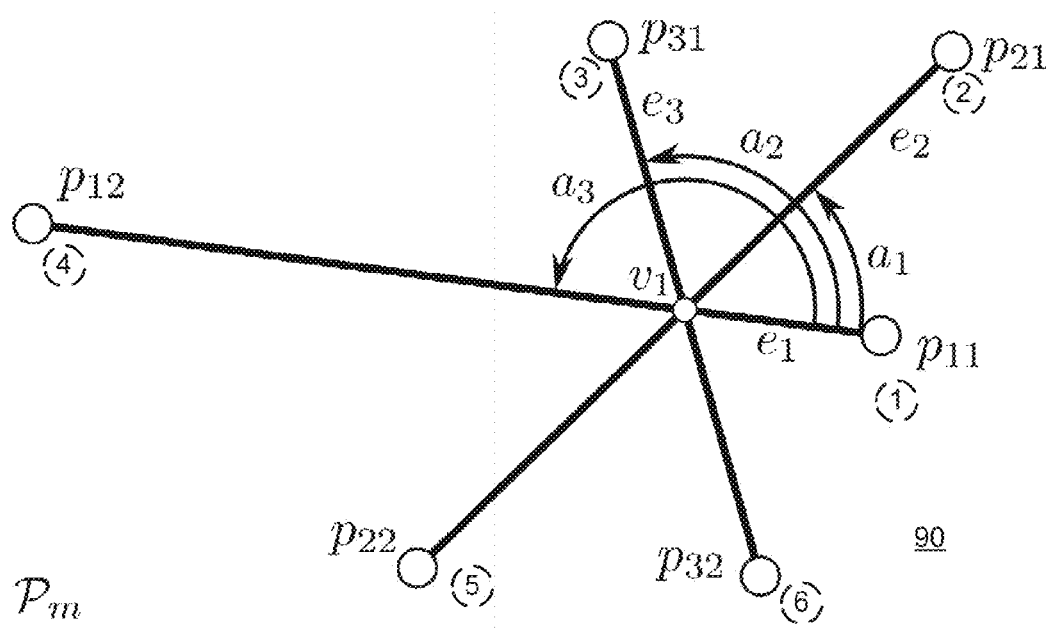
FIG. 4B is a schematic illustration showing a how the seedpoints on an unvisited plane may be ordered according to a particular embodiment.

FIG. 4B schematically illustrates an example implementation of block 68. In FIG. 4B, graph 90 comprises edges $e_1$, $e_2$, and $e_3$. Edges $e_1$, $e_2$, and $e_3$ lie along corresponding line segments having endpoints $(p_{11}, p_{12})$, $(p_{21}, p_{22})$, and $(p_{31}, p_{32})$, respectively. Endpoints $(P_{11}, p_{21})$, $(p_{21}, p_{22})$, and $(p_{31}, p_{32})$, correspond to block 66 seedpoints which correspond to intersections of corresponding block 64 2D contours (not shown in FIG. 4B) with the unvisited plane $P_m$. Starting from arbitrary endpoint and with line segment $e_1$, graph 90 is traversed in order by traversing an edge that forms the smallest counter-clockwise angle with a previously traversed edge, as indicated by arrow $a_1$, $a_2$ and $a_3$. More particularly, seedpoint $p_{11}$ is arbitrarily assigned order value=1. Graph 90 is then traversed from seedpoint $p_{11}$ along edge $e_1$ to vertex $v_1$, where a decision is taken to traverse to edge $e_2$, because edge $e_2$ has the smallest counter-clockwise angle $a_1$ relative to previously traversed edge $e_1$. Accordingly, seedpoint $p_{21}$ is assigned order value=2. In the exemplary implementation of FIG. 4B, this process continues to respectively assign order values 3, 4, 5, 6 to seedpoints $p_{31}$, $p_{12}$, $p_{22}$, $p_{32}$.

Method 60 then proceeds to block 70 which involves using an automatic 2D segmentation process to provide a 2D segmentation of the unvisited plane $P_m$ using the block 66 seedpoints and the block 68 ordering. In particular embodiments, the block 70 2D segmentation involves contouring the unvisited plane $P_m$ to generate one or more contours thereon. Block 70 may comprise contouring the unvisited plane $P_m$ using a fully-automatically Livewire process. In other embodiments, block 70 may use other 2D automatic contouring techniques to obtain contours on the unvisited plane $P_m$. In other embodiments, block 70 may involve automatically generating different types of 2D segmentation information (e.g. labels, probabilities and/or the like) in respect of the unvisited plane $P_m$ based on the block 66 seedpoints and the block 68 ordering.

At the conclusion of block 70, method 60 has used the block 64 2D segmentation information (e.g. contour(s)) obtained for one or more 2D (e.g. planar) surfaces to automatically generate 2D segmentation information (e.g. contour(s)) on an unvisited plane $P_m$. Other techniques may be used to automatically generate 2D segmentation information on an unvisited plane $P_m$ based on the block 64 2D segmentation information (e.g., as alternatives to or supplementary of one or more of steps 66, 68 and 70). Non-limiting examples of such techniques include the following and variants, extensions and adaptations of the following:

Deformable contours, e.g.:
M. Kass, A. Witkin, and D. Terzopoulos, Snakes—Active Contour Models, *International Journal of Computer Vision,* 1(4): 321-331, 1987.

Hybrid methods, e.g.:
J. Liang, T. McInerney, D. Terzopoulos, United Snakes, *Medical Image Analysis,* 10(2), April, 2006, pages 215-233.

Interactive level set methods, e.g.:
Daniel Cremers, Oliver Fluck, Mikael Rousson and Shmuel Aharon, A Probabilistic Level Set Formulation for Interactive Organ Segmentation, *SPIE* 2007.

Ravi Malladi, James A. Sethian, Baba C. Vemuri: Shape Modeling with Front Propagation: A Level Set Approach. *IEEE Trans. Pattern Anal. Mach. Intell.* 17(2): 158-175 (1995)

Paragios, User interactive level set methods for image segmentation, United States Patent Application 20040202369

Graph based methods, e.g.:
Yuri Boykov and Marie-Pierre Jolly. Interactive Graph Cuts for Optimal Boundary & Region Segmentation of Objects in N-D images. In *International Conference on Computer Vision,* (ICCV), vol. I, pp. 105-112, 2001.

Random Walker, as described, for example, in L. Grady. Random walks for image segmentation. *IEEE Trans. Pat. Anal. And Mach. Intel.* 28(11), 1768-1783, 2006.

T. McInerney, SketchSnakes: Sketch-Line Initialized Snakes for Efficient Interactive Medical Image Segmentation, *Computerized Medical Imaging and Graphics,* 32, 2008, pages 331-352.

Cootes and Taylor, Constrained Active Appearance Models, *ICCV,* 2001.

Bram van Ginneken, Marleen de Bruijne, Marco Loog and Max A. Viergever, Interactive Shape Models, *SPIE Medical Imaging,* 2003, 1206-1216.

C. Rother, V. Kolmogorov, A. Blake. GrabCut: Interactive Foreground Extraction using Iterated Graph Cuts. *ACM Transactions on Graphics (SIGGRAPH '04),* 2004.

and/or the like.

The references in this preceding paragraph are hereby incorporated herein by reference.

For the remainder of the description of method 60, unless otherwise stated, it is assumed for ease of description and without loss of generality, that the block 70 2D segmentation information for the unvisited plane $P_m$ comprises one or more 2D segmentation contours.

Method 60 proceeds to block 72 which involves developing a plurality of uncertainty indicators at a corresponding plurality of image regions for the block 70 segmentation contour(s). In the illustrated embodiment, block 72 comprises blocks 74, 76 and 78.

Block 74 involves determining, for each of the block 70 contours, segmentation uncertainty indicators based on local edge strength at image regions corresponding to suitable intervals along the contours. The suitable intervals for which the image regions of the block 74 uncertainty indicators are spaced along the block 70 contours may be based on a coordinate system that spans the space of image data 62. Such a coordinate system may, but need not necessarily have sub-voxel accuracy (i.e. a granularity finer than that of image data 62). The image regions corresponding to the block 74 uncertainty indicators may generally comprise any regions in such a coordinate system. In one particular example, the image regions corresponding to the block 74 uncertainty indicators may be defined to comprise one or more voxels or groups of voxels in image data 62, although this is not necessary.

The block 74 uncertainty indicators are based on an edge strength parameter $f_j$ which is indicative of a likelihood that the $j^{th}$ uncertainty indicator is located at a position $p_j$ that corresponds to an edge image feature. The local edge strength parameter $f_j$ may be computed as a function of a gradient of image data 62 at $p_j$, for example. The gradients of image data 62 at a particular location $p_j$ may be determined on the basis of image data 62 in a vicinity of $p_j$. In embodiments where the block 70 contours are determined using the Livewire 2D segmentation process, the edge strength $f_j$ may be based on the Livewire local edge cost at the position $p_j$. It will be appreciated that the position $p_j$ is a vector quantity. In other embodiments, the edge strength $f_j$ may be determined using other suitable techniques or models indicative of a likelihood that the $j^{th}$ uncertainty indicator is located at a position $p_j$ that corresponds to an edge image feature. It will be appreciated that the block 74 uncertainty indicators are examples of uncertainty indicators based on conformance of the image segmentation determined in block 70 to 3D image data 62.

In some embodiments, block 74 may involve determining, for each image region (e.g. interval) along each block 70 contour, an uncertainty indicator of the form $(p_j, f_j)$ where $p_j$ is the position of the uncertainty indicator and $f_j$ is the local edge strength parameter at $p_j$. In other embodiments, each block 74 uncertainty indicator may comprise additional information based on one or more properties of the block 70 contours and/or image data 62 and may therefore have a form $(p_j, f_j, x_{1j}, x_{2j}, \ldots)$ where $x_{1j}, x_{2j}, \ldots$ represent optional additional information in respect of the $j^{th}$ block 74 uncertainty indicator. In some embodiments, a type of additional information on which the block 74 confidence intervals may be based is a unit normal vector $n_j$ which is normal to the block 70 contour at the location $p_j$ of $j^{th}$ block 74 uncertainty indicator. In such embodiments, each block 74 uncertainty indicator may take the form $(p_j, n_j, f_j)$.

Block 76 involves determining, for each of the block 70 contours, segmentation uncertainty indicators based on local contour stability at image regions corresponding to suitable intervals along the contours. The suitable intervals for which the image regions of the block 76 uncertainty indicators are spaced may be, but need not necessarily be, the same or similar to those of the block 74 uncertainty indicators. The suitable intervals for which the image regions of the block 76 uncertainty indicators are spaced may be based on the same coordinate system as the block 74 uncertainty indicators and the image regions corresponding to the block 76 uncertainty indicators may generally comprise any regions in such a coordinate system. In one particular example, the image regions corresponding to the block 76 uncertainty indicators may be defined to comprise one or more voxels or groups of voxels in image data 62, although this is not necessary.

The block 76 uncertainty indicators are based on a contour stability parameter $t_k$ which is a metric indicative of the stability (e.g. sensitivity to perturbation) of the block 70 contours at a location $p_k$ of the $k^{th}$ uncertainty indicator. In some embodiments, computing the contour stability parameter $t_k$ may comprise: perturbing each block 70 contour at a number of locations to determine a set D of perturbed paths; and, for each uncertainty indicator location $p_k$, evaluating some distance metric between the uncertainty indicator location $p_k$ and the set D of perturbed paths. It will be appreciated that the position $p_k$ is a vector quantity. In one particular embodiment, the set D of perturbed paths may be obtained by perturbing the block 70 contour in a number of locations and, for each perturbation, re-segmenting the unvisited plane Pm while enforcing the location of the perturbed point and the block 66 seedpoints. In one particular embodiment, the distance metric between the uncertainty indicator location $p_k$ and the set D of perturbed paths comprises a maximum (over the set D of perturbed paths) of the shortest Euclidean distance between the uncertainty indicator location $p_k$ and each perturbed path. In another embodiment, the distance metric between the uncertainty indicator location $p_k$ and the set D of perturbed paths comprises an average (over the set D of perturbed paths) of the shortest Euclidean distance between the uncertainty indicator location $p_k$ and each perturbed path. In other embodiments, the contour stability parameter $t_k$ may be determined using other suitable techniques or models indicative of the stability (e.g. sensitivity to perturbation) of the block 70 contours at a location $p_k$ of the $k^{th}$ uncertainty indicator. It will be appreciated that the block 76 uncertainty indicators are examples of uncertainty indicators based on conformance of the image segmentation determined in block 70 to 3D image data 62.

In some embodiments, block 76 may involve determining, for each image region (e.g. interval) along each block 70 contour, an uncertainty indicator of the form $(p_k, t_k)$ where $p_k$ is the position of the uncertainty indicator and $t_k$ is the local contour stability parameter at $p_k$. In other embodiments, each block 76 uncertainty indicator may comprise additional information based on one or more properties of the block 70 contours and/or image data 62 and may therefore have the form $(p_k, t_k, x_{1k}, x_{2k}, \ldots)$ where $x_{1k}, x_{2k}, \ldots$ represent optional additional information in respect of the $k^{th}$ block 76 uncertainty indicator. In some embodiments, a type of additional information on which the block 76 confidence intervals may be based is a unit normal vector $n_k$ which is normal to the block 70 contour at the location $p_k$ of $k^{th}$ block 76 uncertainty indicator. In such embodiments, each block 76 uncertainty indicator may take the form $(p_k, n_k, t_k)$.

Block 78 involves determining, for each of the block 70 contours, segmentation uncertainty indicators based on the seeding strength used to build the particular contour in block 70. The seeding strength of a particular block 70 contour may be modelled by the number of intersections formed among the line segments that connect the block 66 seedpoints (see, for example, intersection point $v_j$ in FIG. 4B) with a relatively large number of intersection points indicative of high seeding strength and a relatively low number of intersection points indicative of low seeding strength. In some embodiments, the block 78 uncertainty indicators may be located at image regions corresponding to suitably spaced intervals along the line segments between corresponding block 66 seedpoints, although this is not necessary. In other embodiments, the block 78 uncertainty indicators may be located at other regions, such as at suitably spaced intervals along the block 70 contours, which may be the same or similar to those of the block 74 uncertainty indicators. The image regions of the block 78 uncertainty indicators may be defined on the same coordinate system as the block 74 uncertainty indicators and the image regions corresponding to the block 78 uncertainty indicators may generally comprise any regions in such a coordinate system. In one particular example, the image regions corresponding to the block 78 uncertainty indicators may be defined to comprise one or more voxels or groups of voxels in image data 62, although this is not necessary.

The block 78 uncertainty indicators are based on a seeding parameter $r_l$ which is indicative of the seeding strength of a particular block 70 contour. The seeding parameter $r_l$ may be a function of the number of intersection points among the line segments that connect the block 66 seedpoints for a particular block 70 contour (see, for example, intersection point $v_l$ in FIG. 4B). The seeding parameter $r_l$ may be a function which compares the number of such seedpoint-line-segment intersections for a block 70 contour to one or more thresholds. A relatively low number of seedpoint-line-segment intersections may be indicative of a relatively high uncertainty and a correspondingly high value for the seeding parameter $r_l$. Conversely, a relatively high number of seedpoint-line-segment intersections may be indicative of a relatively low uncertainty and a correspondingly low value for the seeding parameter $r_l$. In one particular embodiment, the number of seedpoint-line segment indicators on a block 70 contour is compared to a threshold number (e.g. 1 or 2). Uncertainty indicators having image regions (e.g. positions $p_l$) on the seedpoint-line segments associated with that block 70 contour may then be assigned one value of seeding parameter $r_l$ if the number of seedpoint-line-segment intersections for the block 70 contour is less than the threshold and a different (e.g. lower) value of seeding parameter $r_l$ if the number of seedpoint-line-segment intersections on the block 70 contour is greater than the threshold. In other embodiments, the seeding parameter $r_l$ may be determined using other suitable techniques or models indicative of the number of seedpoint-line-segment intersections of the block 70 contours at a location $p_l$ of the $l^{th}$ uncertainty indicator. It will be appreciated that the block 78 uncertainty indicators may be examples of uncertainty indicators based on a model representing an efficacy of trusted segmentation information from which the image segmentation in block 70 was determined (i.e., where the 2D segmentation information obtained in step 64 comprises trusted segmentation information (e.g., because it is manually or semi-automatically generated), the number of seeds from which the block 70 uncertainty indicators are determined reflects an amount of trusted segmentation information).

In some embodiments, block 78 may involve determining, for each image region (e.g. interval) along a line segment connecting block 66 seedpoints, an uncertainty indicator of the form $(p_l, r_l)$ where $p_l$ is the position of the uncertainty indicator and $r_l$ is the seeding strength parameter. It will be appreciated that the position $p_l$ is a vector quantity. In other embodiments, each block 78 uncertainty indicator may comprise additional information based on one or more properties of the block 70 contours and/or image data 62 and may therefore have the form $(p_l, r_l, x_{1l}, x_{2l}, \ldots)$ where $x_{1l}, x_{2l}, \ldots$ represent optional additional information in respect of the $l^{th}$ block 78 uncertainty indicator. In some embodiments, a type of additional information on which the block 78 confidence intervals may be based is a unit normal vector $n_l$ which is in the plane of the block 70 contour at the location $p_l$ of $l^{th}$ block 78 uncertainty indicator and which may be oriented in a direction orthogonal to the line seedpoint-line segment associated with the location $p_l$. In such embodiments, each block 78 uncertainty indicator may take the form $(p_l, n_l, r_l)$.

The procedures of blocks 66 through 72 establish a 2D segmentation (e.g. contours) on the unvisited plane $P_m$ together with corresponding uncertainty indicators. Blocks 66 through 72 may be repeated (in a loop 79) for a number of unvisited planes to thereby construct a set of corresponding 2D segmentations (e.g. contours) and corresponding uncertainty indicators. In one embodiment, blocks 66 through 72 may be repeated for a dense set of planes parallel to arbitrary plane $P_m$ and the 2D segmentations (e.g. contours) of these unvisited planes may be interpolated to generate a 3D image segmentation.

In some embodiments, blocks 66 through 70 may be repeated in a loop (not shown in FIG. 2) to establish 2D segmentations (e.g., contours) for a plurality of unvisited planes, and, after this loop has terminated or in parallel with this loop, corresponding uncertainty indicators generated for the set of 2D segmentations in block 72. In some embodiments, a 3D segmentation is generated based on a plurality of 2D segmentations generated by iterations of blocks 66 through 70, and uncertainty indicators generated for the 3D segmentation in block 72.

Block 80 comprises identifying a low-confidence region in image data 62 which corresponds to a portion of the previously determined segmentation(s). In some embodiments, the block 80 low-confidence region may comprise a plane in image data 62. In informal terms, block 80 may be directed to identifying a low-confidence image region (e.g. plane) that lies closest to the portions of the segmentation(s) having the greatest uncertainty (e.g. strongest uncertainty indicators). In the illustrated embodiment, determining the block 80 low-confidence plane involves an optimization procedure which selects a block 80 low-confidence plane from among a plurality of candidate planes. Such an optimization procedure may involve evaluating an objective function for the various candidate planes. In one particular embodiment, for each candidate plane P, with a normal $n_P$ and offset $d_P$ from an origin of image data 62, an example objective function E(P) may be given by:

$$E(P) = \Sigma_{i \in UI} s_i E_{UI}(i,P) \qquad (2)$$

Where $s_i$ is the strength of the $i^{th}$ uncertainty indicator which may be computed as some combination (e.g. a linear combination) of the uncertainty strength parameters $f_i$, $t_i$ and $r_i$ discussed above. Where $E_{UI}(i,P)$ is the cost contribution associated with the $i^{th}$ uncertainty indicator. $E_{UI}(i,P)$ may be relatively high if the plane P is relatively proximate to the $i^{th}$ uncertainty indicator and relatively low if the plane P is relatively distant from the $i^{th}$ uncertainty indicator. $E_{UI}(i,P)$ may also be relatively high if plane P is relatively parallel to the normal vectors $n_i$ of the $i^{th}$ uncertainty indicator and relatively low if plane P is relatively orthogonal to the normal vectors $n_i$ of the $i^{th}$ uncertainty indicator.

In one non-limiting example embodiment, $E_{UI}(i,P)$ may be defined as:

$$E_{UI}(i,P) = q_P(i) + (1 - q_P(i)) L(d(p_i, P)) \qquad (3)$$

Where:

- $p_i$ represents the position of the $i^{th}$ uncertainty indicator (which is a vector quantity).
- $q_P(i) = (n_i \cdot n_P)^2$ — i.e. a "dot product" operation which describes how similar the normal $n_P$ of candidate plane P is to the normal $n_i$ of the $i^{th}$ uncertainty indicator ($n_P$, $n_i$ being vector quantities). The more orthogonal the normals $n_P$, $n_i$ are to one another, the lower the value of $q_P(i)$ and, consequently, equation (3) yields a value of $E_{UT}$ closer to $L(d(p_i,P))$.
- $d(p_i,P)$ is a distance metric which provides a distance between the position $p_i$ of the $i^{th}$ uncertainty indicator and the candidate plane P. In one particular embodiment, $d(p,P) = |p \cdot n_P - d_P|$, where $p \cdot n_P$ is a dot product operation and $d_P$ is an offset of the plane P from the origin of image data 62.
- $L: [0,\infty) \to [0,1)$ is a logistic shaped function used to reduce the influence on the optimization of uncertainty indicators spaced from P.

The block 80 objective function E(P) may be maximized (or minimized) with respect to P using any suitable optimization algorithm, of which there are many known in the art. The candidate plane P corresponding to the objective function minimum (or maximum) may be selected as the block 80 low-confidence plane. In some embodiments, multiple optimizations may be performed using different initial planes P and the candidate plane with the highest (or lowest) objective function value may be selected as the block 80 low-confidence plane—i.e. to avoid issues with local extrema during optimization. In some embodiments, block 80 may output a plurality of low-confidence planes which may be ranked in order of uncertainty (e.g. cost). In such embodiments, identifying a plurality of low-confidence planes may involve performing a series of optimizations and, for each of the second and subsequent iterations, artificially assigning low strengths to uncertainty indicators in a vicinity of a previously identified low-confidence plane in a manner similar to that discussed above for block 40. This artificial assignment of low strengths to uncertainty indicators may avoid outputting a plurality of low-confidence planes that are undesirably close to one another.

After the block 80 identification of the low-confidence plane(s), method 60 proceeds to block 82 which involves obtaining user-assisted 2D segmentation information in respect of the block 80 low-confidence plane(s). The block 82 user-assisted 2D segmentation information for the block 80 low-confidence plane(s) may generally comprise any type of segmentation information, including: contours, labels, probabilities, and/or the like. The block 82 process for generating user-assisted segmentation information for the block 80 low-confidence plane(s) may comprise a manual segmentation process or a semi-automatic segmentation process. In one particular embodiment, block 82 may comprise semi-automatically generating 2D segmentation contour(s) for the block 80 low-confidence plane(s) using an interactive 2D segmentation technique, such as the 2D Livewire algorithm, for example.

After block 82, method 60 returns to block 66. Block 66 may be similar to that described above and may involve seeding seedpoints on the object boundaries/edges of an unvisited plane $P_m$ at intersections of segmentation edges (e.g. contours) of the block 64 2D segmentations. However, for the second and subsequent iterations of block 66, the object boundaries/edges of the unvisited plane $P_m$ are additionally seeded at locations where the plane $P_m$ is intersected by the segmentation edges (e.g. contours) obtained in block 82—i.e. the user-assisted segmentation of the block 80 low-confidence plane(s). As is apparent from the return to block 66, method 60 includes loop 84, which in the illustrated embodiment comprises blocks 66, 68, 70, 72, 80 and 82. Loop 84 may be repeated, with user input provided at block 82 of each iteration accumulating, such that in successive iterations of loop 84, block 66 involves seeding the segmentation boundaries of the unvisited plane $P_m$ using increasing amounts of user input.

Figure 5:
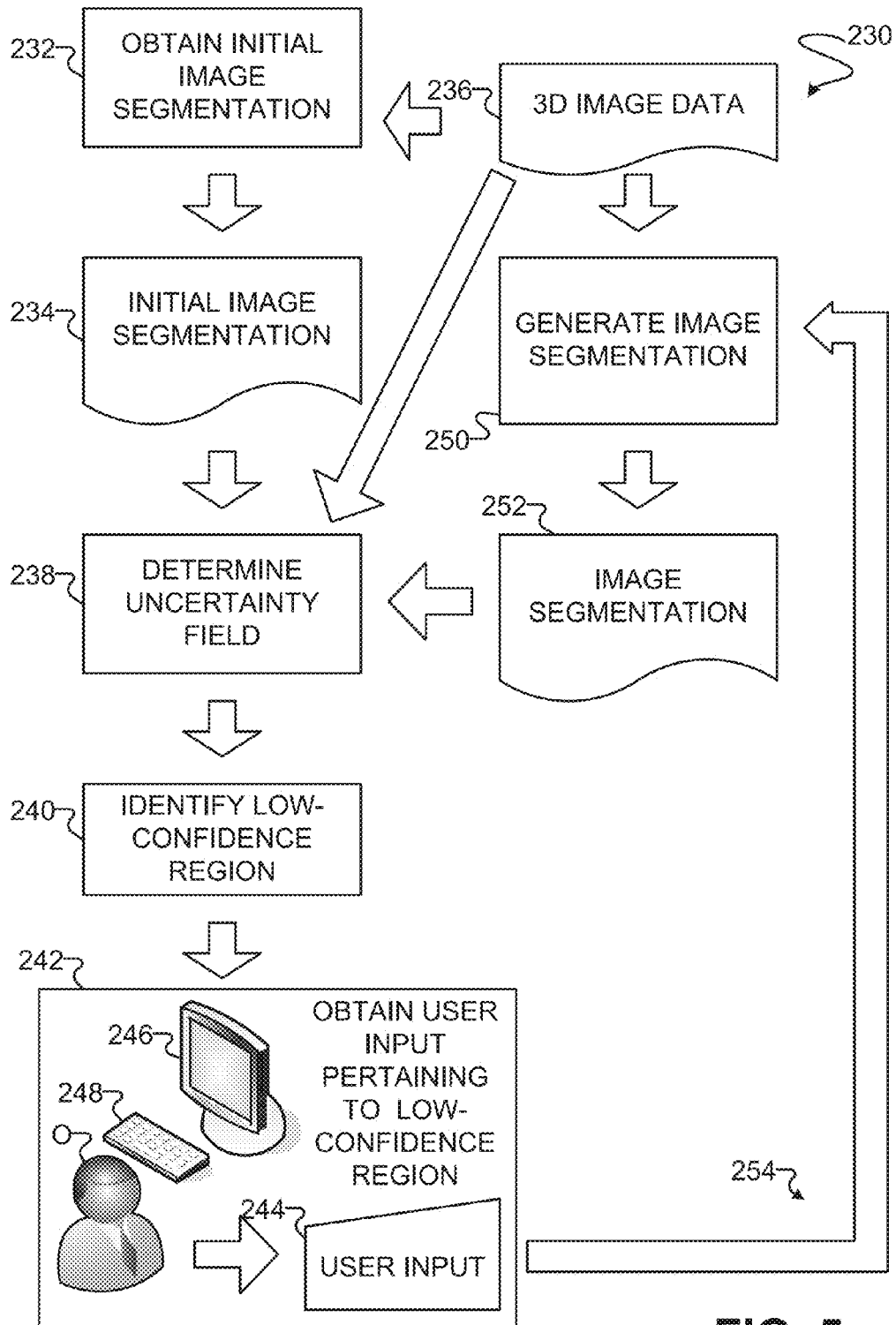
FIG. 5 is a flowchart showing a method for 3D image segmentation according to another example embodiment.

FIG. 5 is a flowchart of a method 230 for segmentation of 3D image data 236 according to another example embodiment. In many respects, method 230 is similar to methods 30, 60 described above. For the sake of brevity, the following description of method 230 focuses on the differences between method 230 and methods 30, 60.

Method 230 begins in block 232, which involves obtaining an initial image segmentation 234 for 3D image data 236. Block 232 may be substantially similar to block 32 described above. Segmentation 234 may be expressed as a segmentation classifier y(x) defined over the set of coordinates $x \in X$, where X spans the space of 3D image data 236. The segmentation classifier y(x) represents a general form of segmentation information in respect of the point x, which may include, for example: a label that the point x belongs to one of a set of image segments; probabilities that the point x belongs to each one of a set of image segments; and/or the like. The set of coordinates X may have an accuracy that is the same as or finer than the size of voxels in image data 236.

Method 230 then proceeds to block 238, which involves determining an uncertainty field U(x) for the set of coordinates X. The block 238 uncertainty field may assign a scalar uncertainty value to every coordinate x in the set of coordinates X. In some embodiments, the block 238 uncertainty values may be calculated and stored (e.g. in a look up table) in manner that they may be indexed by their respective coordinates. In some embodiments, the block 238 uncertainty field may be determined in the form of a suitable equation, operator and/or the like which may be computed as and when needed to determine the uncertainty field value for a given set of coordinates.

The values of the block 238 uncertainty field reflect uncertainty (e.g. a lack of confidence) that current segmentation 234, 252 correctly characterizes corresponding image regions of 3D image data 236. That is, uncertainty field U(x) reflects a lack of confidence in a particular segmentation classifier y(x) over the set of coordinates X. It will be appreciated that the value of uncertainty field U(x) at a coordinate x in the set of coordinates X expresses the strength of a segmentation uncertainty indicator for segmentation classifier y(x) at the image regions corresponding to coordinate x in 3D image data 236. In some embodiments, the block 238 uncertainty field U may be determined in accordance with a formula of the form:

$$U(x) = \lambda_A U_A(x) + \lambda_B U_B(x) + \lambda_C U_C(x) + \ldots \qquad (4)$$

where:

- $U_A(x), U_B(x), U_C(x), \ldots$ are functions which model uncertainty contributions based on different properties of one or any combination of the current segmentation 234, 252, image data 236, and trusted segmentation information; and
- $\lambda_A, \lambda_B, \lambda_C, \ldots$ represent weighting factors for the respective uncertainty model functions $U_A(x), U_B(x), U_C(x), \ldots$.

Uncertainty model functions $U_A(x), U_B(x), U_C(x), \ldots$ can be designed to model uncertainty based on a variety factors, such as:

conformance of current image segmentation 234,252 to 3D image data 236;

conformance of current image segmentation 234,252 to another image segmentation for 3D image data 236;

the quality (e.g., resolution, contrast, edge strength, noise, image artefacts, partial volume effects, intensity heterogeneity etc.) of image data 236;

conformance of current image segmentation 234,252 to one or more expected image segmentation properties (e.g., 3D shape similarity of current image segmentation 234,252 to a reference shape, 2D similarity of a cross-section of current image segmentation 234,252 to a reference cross-section, surface geometry similarity of current image segmentation 234,252 (or a portion thereof) to a reference surface geometry (such as smoothness, for example), etc.);

a model of the efficacy of trusted segmentation information from which current image segmentation 234,252 was determined;

any combination of the above; and/or the like.

By way of one particular and non-limiting example, uncertainty model functions $U_A(x)$, $U_B(x)$, $U_C(x)$, . . . may be designed to model features similar to any one or more of those described above for the various block 72 confidence indicators (see FIG. 3)—e.g. a model function $U_A(x)$ which models the boundary/edge strength of the current segmentation 234, 252 (which is an aspect of conformance of current image segmentation 234,252 to 3D image data 236); a model function $U_B(x)$ which models the stability of the current segmentation 234, 252 to perturbation (which is another aspect of conformance of current image segmentation 234,252 to 3D image data 236); and a model function $U_C(x)$ which models the seeding strength of the current segmentation 234, 252 (which is reflects a model of an efficacy of trusted segmentation information from which current image segmentation 234,252 was determined).

In some embodiments the equation (4) uncertainty field U(x) may comprise additional or alternative uncertainty model functions $U_A(x)$, $U_B(x)$, $U_C(x)$, . . . which may include any one or more of the following non-limiting examples.

An entropy model function $U_E(x)$ which may be used where the segmentation classifier y(x) comprises probabilities $p_L(x)$, $p_M(x)$, $p_N(x)$ . . . of the point x being respectively labelled as image segment L, M, N . . . . Such an entropy model function may model the uncertainty of the current segmentation 234, 252. Such an entropy model function may assign: relatively high uncertainty values $U_E$ to point x where the probabilities $p_L(x)$, $p_M(x)$, $p_N(x)$ . . . are relatively equal (i.e. where the segmentation is unsure about what label to apply to point x); and relatively low uncertainty values $U_E$ to point x where one of the probabilities $p_L(x)$, $p_M(x)$, $p_N(x)$ . . . is relatively high compared to the others (i.e. where the segmentation is sure about what label to apply to point x). It will be appreciated that entropy model function $U_E(x)$ models uncertainty based on conformance of current image segmentation 234,252 to an expected image segmentation property, namely that the segmentation is expected to indicate a single characterization to the exclusion of mutually exclusive alternative characterizations.

A regional model function $U_R(x)$ which may model how well the intensity of image data 236 at a particular point x conforms to intensity distributions of the pixels inside and outside of the current segmentation 234, 252. Such a model may: fit Gaussian distributions (referred to as inside and outside distributions) to the pixel values (e.g. intensity values) considered by the current segmentation 234, 252 to be inside and outside the current segmentation; compute a probability ($P_{IN}(x)$, $P_{OUT}(x)$) that a point x belongs to each of the inside and outside distributions; and then compare this probability to the segmentation classification (IN or OUT) assigned to the point x. If the segmentation classification (IN or OUT) assigned to the point x is matched by a correspondingly high probability ($P_{IN}(x)$ or $P_{OUT}(x)$), then the regional model function uncertainty $U_R(x)$ may be assigned a relatively low value. If on the other hand, the segmentation classification (IN or OUT) assigned to the point x is matched by a correspondingly low probability ($P_{IN}(x)$ or $P_{OUT}(x)$), then the regional model function uncertainty $U_R(x,y)$ may be assigned a relatively high value. It will be appreciated that regional model function $U_R(x)$ models uncertainty based on conformance of current image segmentation 234,252 (pixels inside and outside of current segmentation 234,252) to 3D image data 236 (intensity distributions for pixels inside and outside of the structure which current segmentation 234,252 ostensibly delineates).

A smoothness model function $U_R(x)$ which may model the smoothness of the current segmentation 234, 252. Assuming that the features being segmented from image data 236 are relatively smooth (as may be the case with soft organ tissue in medical imaging, for example), then relatively smooth segmentations may be assigned relatively low smoothness uncertainty model value $U_R(x)$ and relatively jagged segmentations may be assigned relatively high smoothness uncertainty model value $U_R(x)$. In one particular embodiment, the smoothness model function $U_R(x)$ is based on the observation that smooth surfaces have less surface area than jagged surfaces and may therefore involve a surface integral of the segmentation surface in a neighborhood around the point x. It will be appreciated that smoothness model function $U_R(x)$ models uncertainty based on conformance of current image segmentation 234,252 to an expected image segmentation property, namely that the segmentation is relatively smooth.

An image quality model $U_Q(x)$ which may model the quality of the image data (e.g., contrast, resolution, edge strength, noise, image artefacts, partial volume effects, intensity heterogeneity etc.), where $U_Q(x)$ is assigned relatively high uncertainty when image quality is relatively low, and vice versa.

An object topology model $U_{Conn}(x)$ which may model how well the current segmentation 234,252 conforms to a particular topology (e.g., a single connected and filled body, plural disconnected bodies, a body having one or more voids, etc.) Conformance to the expectations results in low uncertainty, whereas deviation for this conformance results in high uncertainty. It will be appreciated that object topology model $C_{Conn}(x)$ models uncertainty based on conformance of current image segmentation 234,252 to an expected image segmentation property.

A segmentation conflict model $U_{conflict}(x)$ which may model the degree of agreement amongst different sources of information about what constitutes a correct segmentation. The higher the agreement the lower the uncertainty, and vice versa. An example of a disagreement is when, according to image data (e.g., intensity distribution), a segmentation should have one value, but according to an expected segmentation property (e.g., a shape prior), the segmentation should have another value.

The values of the block 238 uncertainty field may have a range of possible values (e.g. in a normalized range [0,1]). A value associated with the block 238 field at a particular set of coordinates may be referred to as the strength of the uncertainty field at that particular set of coordinates. Relatively low and relatively high uncertainty strengths may be respectively indicative of relatively high and low levels of confidence in the current segmentation at a particular set of coordinates. The values of the block 238 uncertainty field may, in some embodiments, depend on the method used to generate current segmentation 234, 252.

After the uncertainty field has been determined in block 238, method 230 proceeds to block 240 which involves identifying a low-confidence region based on the block 238 uncertainty field. The block 240 low-confidence region is then recommended to operator O for user segmentation input 244 in block 242. Since the block 238 uncertainty field assigns an uncertainty value to each coordinate x, it is conceivable that block 240 may involve identifying the one coordinate of the block 238 uncertainty field with the highest uncertainty value to be the block 240 low-confidence region and suggesting that the operator O provide user segmentation input 244 in respect of that one coordinate. While this approach may work, it may be inefficient, as it may require examining a large number of individual and disjointed coordinates in order to complete method 230 in a satisfactory manner.

Accordingly, instead of identifying one single coordinate for user segmentation input, block 240 may identify a larger low-confidence region which may be presented to operator O in block 242 as a so-called "batch query" where operator O can provide user segmentation information 244 in respect of a "batch" of coordinates. A convenient type of region to identify as a low-confidence region in block 240 and to present to operator O as a batch query in block 242 is a 2D surface, such as a plane, for example. While method 230 is not limited to the block 240 low-confidence region being two-dimensional or planar, a planes and some other types of two-dimensional surfaces are convenient for at least the reasons that they are relatively easy to present to operator O on display 246 for the purposes of presenting the batch query and that it is relatively easy for operator O to use a semi-automated 2D segmentation technique on a plane or other simple two-dimensional surface to provide user segmentation input 244.

For the case that block 240 involves identifying a low-confidence plane, then block 240 may attempt to identify a plane (e.g. from among a set of candidate planes or otherwise) with maximal uncertainty—i.e. a plane that is proximate to (e.g., that intersects or is near to) the coordinates with the highest values of the block 238 uncertainty field U(x). The plane with maximal uncertainty may be defined as $\text{argmax}_P (U_P)$ where $U_P$ may be given by:

$$U_P = \iint_P U(x) dA \quad (5)$$

where U(x) represents the block 238 uncertainty field at point x and the equation (5) integral is performed over the area of a candidate plane P, with the condition that U(x) is limited to the space X of x and zero-valued elsewhere. It will be appreciated that while U(x) has been treated herein as a function defined over a continuous range of values, embodiments may implement U(x) as a function defined over a range of discrete values, and that discrete operators (e.g., Riemann sums) may be applied to U(x) in place of continuously defined operators (e.g., integrals) without loss of generality.

At the conclusion of block 240, method 230 identifies a low-confidence region (e.g. a low-confidence plane) that is proximate to the most uncertainty in the block 238 uncertainty field and then recommends this low-confidence region for user segmentation input 244 in block 242. In some embodiments, block 240 may involve identifying a plurality of low-confidence regions (e.g. planes). The identification of multiple low-confidence regions may be performed in a manner analogous to that of block 40 or block 80 described above, modified for application to the block 238 uncertainty field.

Block 242 may be substantially similar to block 42 discussed above and may involve obtaining user segmentation input 244 for the block 240 low-confidence region. Any suitable image segmentation technique may be used to obtain user segmentation input 244 in block 242. Where the block 240 low-confidence region is a plane, block 242 may comprise obtaining user segmentation input 244 that constructs a 2D image segmentation on the plane. In some embodiments, the user segmentation input 244 obtained in block 242 may comprise semi-automatically generated segmentation information (e.g. a semi-automatically generated 2D segmentation).

Method then proceeds to block 250 which may be substantially similar to block 50 described above and may involve generating an updated 3D image segmentation 252 of image data 236 which takes into account user segmentation input 244. The block 250 image segmentation may also be based on previous segmentations of image data 236.

It will be appreciated from the discussion above that the method by which the low-confidence region is identified in block 240 may be adapted so that the user segmentation input 244 obtained in block 242 results in an optimal or near-optimal improvement in image segmentation 252 when image segmentation 252 is generated in block 250. At the conclusion of block 250, an inquiry (not explicitly shown) may optionally be conducted to determine if the newly generated image segmentation 252 is acceptable. This inquiry may involve displaying the newly generated image segmentation 252 on display 246 and allowing operator O to visually inspect image segmentation 252 and to indicate the acceptability of the newly generated image segmentation 252 using user interface 248. If the newly generated image segmentation 252 is acceptable, then method 230 may be concluded.

If the block 250 inquiry determines that the newly generated image segmentation 252 is not acceptable, then method 230 proceeds to block 238 which involves re-determining an uncertainty field. In the second and subsequent iterations of block 238, the block 238 uncertainty field is determined in relation to newly generated image segmentation 252 (as opposed to initial image segmentation 234 as described above). As is apparent from the return to block 238, method 230 includes loop 254, which in the illustrated embodiment comprises blocks 238, 240, 242 and 250. Loop 254 may be repeated, with user segmentation data 244 accumulated in each iteration, such that in successive iterations of loop 254, block 250 generates image segmentation 252 using increasing amounts of optimal user segmentation input 244. In some embodiments, block 240 may comprise terminating method 230 if the identified low-confidence plane intersects with an amount of uncertainty that is less than a threshold amount.

Figure 5A:
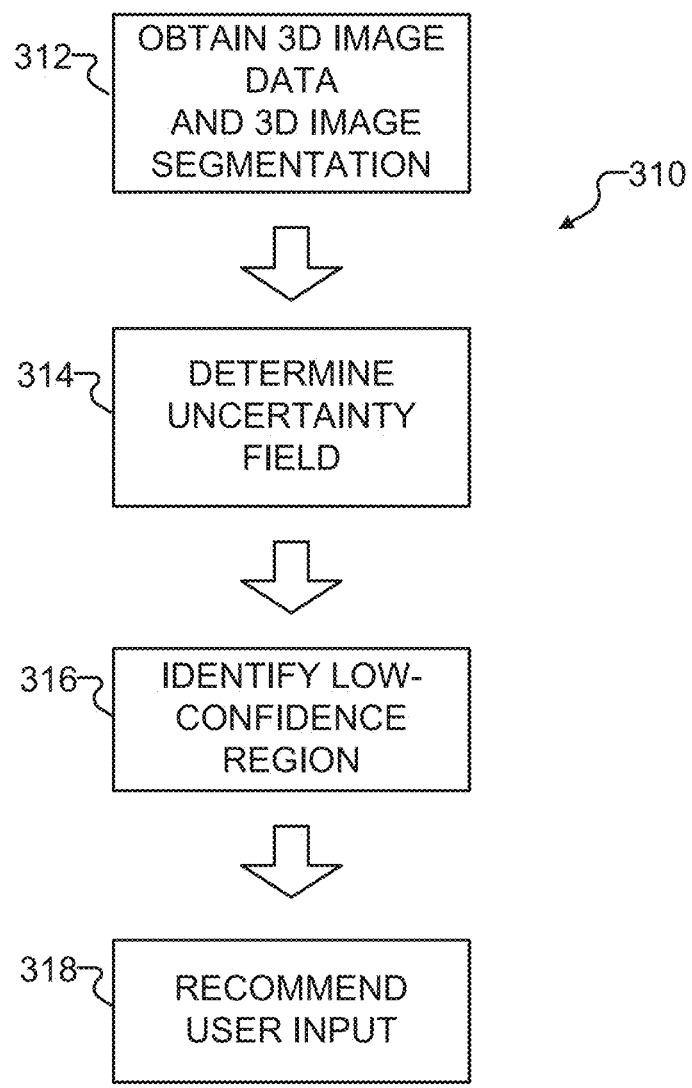
FIG. 5A is a flowchart showing a method for recommending optimal user input for a 3D image segmentation according to an example embodiment.

FIG. 5A is a flowchart showing a method 310 for recommending a region (e.g. an optimal image region and in some embodiments a planar image region) for user segmentation input in a 3D image segmentation process according to an example embodiment. Method 310 comprises a number of processes which are similar to those of 3D segmentation method 230 described above. Method 310 begins in block 312 which involves obtaining 3D image data and a corresponding 3D image segmentation. The block 312 3D image segmentation may be obtained as a part of a 3D segmentation process in which method 310 forms a part. The block 312 image segmentation may be obtained using any suitable technique, including generating the block 312 image segmentation automatically, semi-automatically or manually. In some embodiments, block 312 comprises obtaining a 3D image segmentation from an external source.

Method 310 then proceeds to block 314 which involves determining an uncertainty field for the block 312 3D segmentation. Obtaining the block 314 uncertainty field may be substantially similar to obtaining the uncertainty field in block 238 described above and may be based on the block 312 3D segmentation and the block 312 3D image data. Method 310 then proceeds to block 316 which involves identifying one or more low-confidence regions for the block 312 3D segmentation. Identifying low-confidence region(s) in block 316 may be substantially similar to identifying low-confidence region(s) in block 240 discussed above and may involve recommending a low-confidence plane based on the intersection of the plane with the block 314 uncertainty field.

Method 310 then proceeds to block 318 which involves recommending one or more of the block 316 low-confidence region(s) to be an optimal region for receiving user segmentation input.

Figure 6:
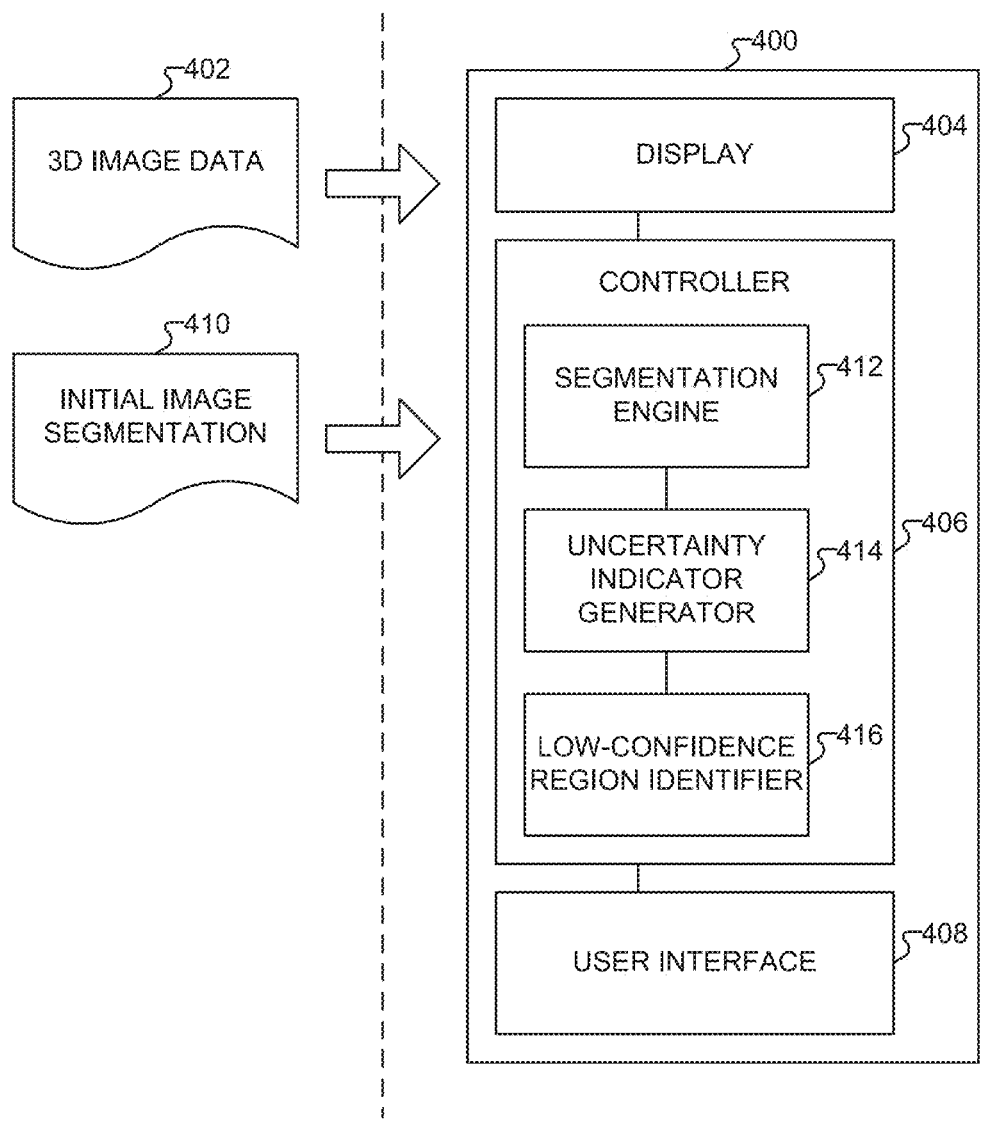
FIG. 6 is a schematic diagram of a system according to an example embodiment.

FIG. 6 shows a schematic diagram of an system 400 for segmenting 3D image data 402 according to an example embodiment. System 400 and the components thereof may be configured to perform all of part of one or more of methods 30, 60, 110, 230, and 310, as well as combinations, subcombinations, and variants thereof. System 400 comprises a display 404, a controller 406, and a user interface 408. System 400 is configured to receive 3D image data 402, and, optionally, initial image segmentation 410, which comprises a segmentation of 3D image data 402.

Controller 406 comprises segmentation engine 412, uncertainty indicator 414 and low-confidence region identifier 416. Segmentation engine 412 may be configured to generate initial 3D image segmentation 410 based on 3D image data 402 automatically or semi-automatically based on user input received at user interface 408.

Uncertainty indicator generator 414 is configured to generate uncertainty indicators for image segmentations (e.g., image segmentation 410) at each of a plurality of image regions of 3D image data 402. In some embodiments, uncertainty indicator generator 414 is configured to perform one or more of block 38 of method 30, block 72 of method 70, block 114 of method 110, block 238 of method 230, and block 314 of method 310, for example. Uncertainty indicator generator 414 may be configured to generate uncertainty indicators according to any of the example techniques described herein, as well as according to other techniques, including those which may developed in the future.

Low-confidence region identifier 416 is configured to identify one or more low-confidence region in the 3D image data 402 based at least in part on proximity of the low-confidence region to the image regions and strengths of the corresponding uncertainty indicators. In some embodiments, low-confidence region identifier 416 is configured to identify a low-confidence region from among a plurality of candidate regions. For example, block 40 may involve identifying a low-confidence region by performing an optimization routine which maximizes (or minimizes) an objective function (known variously in the art of optimization as a cost function, energy function, etc.) across the set of candidate regions. In some embodiments, low-confidence region identifier 416 is configured to compute, for each of a plurality of candidate regions, a value of an objective function based at least in part on proximity of the candidate region to the image regions and the strengths of the corresponding uncertainty indicators. Low-confidence region identifier 416 may be configured to compute values for an objective function whose value for a candidate region is based on the proximity of the candidate region to each of the image regions scaled according to the strength of the corresponding uncertainty indicator. Low-confidence region identifier 416 may be configured to perform one or more of block 40 of method 30, block 116 of method 110, block 80 of method 60, block 240 of method 230, and block 316 of method 310, for example. Low-confidence region identifier 416 may be configured to identify one or more low-confidence regions generate uncertainty indicators according to any of the example techniques described herein, as well as according to other techniques, including those which may developed in the future.

Controller 406 is configured to obtain user input, such as user segmentation input, for low confidence regions identified by low-confidence region identifier 416. For example, controller 406 may be configured to cause display 404 to prompt a user to supply segmentation information for a low-confidence region identified by low-confidence region identifier 416. In some embodiments, controller 406 is configured to cause display 404 to display a portion of 3D image data 402 corresponding to a low-confidence region identified by low-confidence region identifier 416, and to obtain from user interface 408 a user segmentation of the displayed image data input. Controller 406 may be configured to control display 404 and obtain input from user interface 408 to achieve the results of one or more of block 42 of method 30, block 118 of method 110, block 82 of method 60, block 242 of method 230, and block 318 of method 310, for example.

Segmentation engine 412 is configured to 50 generate an image segmentation of 3D image data 402 based at least in part on user segmentation input obtained by controller 406 via user interface 408. In some embodiments, segmentation engine 412 is configured to generate the image segmentation based on information from one or more previous segmentations of image data 402. Segmentation engine 412 may be configured to generate an image segmentation of 3D image data 402 according to any suitable 3D image segmentation algorithm, including known and future image segmentation algorithms. Segmentation engine 412 may be configured to perform one or more of block 50 of method 30, blocks 66, 68 and 70 of method 60, and block 250 of method 230, for example.

Controller 406 and component thereof may comprise hardware, software, firmware or any combination thereof. For example, controller 406 may be implemented on a programmed computer system comprising one or more processors, user input apparatus, displays and the like. Processors may comprise microprocessors, digital signal processors, graphics processors, field programmable gate arrays, and/or the like. Components of controller 406 may be combined or subdivided, and components of controller 406 may comprise sub-components shared with other components of controller 406. Components of system 400, including components of controller 406, may be physically remote from one another. For example, controller 406 may be instantiated in a programmed server computer which communicates with display 404 and user interface 408 via the Internet or another network.

Where a component is referred to above (e.g., a display, controller, user interface, segmentation engine, uncertainty indicator generator, optimizer, etc.), unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." Where the context permits, words in the above description using the singular or plural number may also include the plural or singular number respectively. The word "or," in reference to a list of two or more items, covers all of the following interpretations of the word: any of the items in the list, all of the items in the list, and any combination of the items in the list.

The above detailed description of example embodiments is not intended to be exhaustive or to limit this disclosure and claims to the precise forms disclosed above. While specific examples of, and examples for, embodiments are described above for illustrative purposes, various equivalent modifications are possible within the scope of the technology, as those skilled in the relevant art will recognize.

These and other changes can be made to the system in light of the above description. While the above description describes certain examples of the technology, and describes the best mode contemplated, no matter how detailed the above appears in text, the technology can be practiced in many ways. As noted above, particular terminology used when describing certain features or aspects of the system should not be taken to imply that the terminology is being redefined herein to be restricted to any specific characteristics, features, or aspects of the system with which that terminology is associated. In general, the terms used in the following claims should not be construed to limit the system to the specific examples disclosed in the specification, unless the above description section explicitly and restrictively defines such terms. Accordingly, the actual scope of the technology encompasses not only the disclosed examples, but also all equivalent ways of practicing or implementing the technology under the claims.

From the foregoing, it will be appreciated that specific examples of apparatus and methods have been described herein for purposes of illustration, but that various modifications, alterations, additions and permutations may be made without departing from the practice of the invention. The embodiments described herein are only examples. Those skilled in the art will appreciate that certain features of embodiments described herein may be used in combination with features of other embodiments described herein, and that embodiments described herein may be practised or implemented without all of the features ascribed to them herein. Such variations on described embodiments that would be apparent to the skilled addressee, including variations comprising mixing and matching of features from different embodiments, are within the scope of this invention.

As will be apparent to those skilled in the art in light of the foregoing disclosure, many alterations and modifications are possible in the practice of this invention without departing from the spirit or scope thereof. For example:
  a low-confidence region need not be contiguous;
  in some embodiments, the uncertainty field of method 230 is a vector field;
  while in example method 60 the block 64 2D segmentation information comprises 2D points on a plane, the location of these 2D points in 3D space may be obtained from definition of the plane to yield 3D points, which can be used as input to various 3D segmentation methods;
  systems, computer program products and corresponding methods may be embodied in the form of plug-in modules to existing 3D image segmentation software and systems.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A computer-implemented method for improving an initial segmentation of 3D digital image data to obtain an updated segmentation of the 3D digital image data, the method comprising:
  obtaining an initial segmentation of a 3D digital image comprising corresponding 3D image data;
  storing the initial segmentation of the 3D digital image data in memory accessible to a computer;
  for each of a plurality of image regions within the 3D digital image data, associating an uncertainty indicator for the initial image segmentation with the image region and assigning, by the computer, a strength to the uncertainty indicator;
  identifying, by the computer, a low-confidence region in the 3D digital image data based at least in part on proximity of the low-confidence region to the image regions and strengths of the corresponding uncertainty indicators;
  obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
  updating, by the computer, the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
  storing the updated segmentation of the 3D digital image data in the memory accessible to the computer.

2. The method of claim 1 wherein identifying, by the computer, the low-confidence region in the 3D digital image data comprises computing, for each of a plurality of candidate regions, a value of an objective function based at least in part on proximity of the candidate region to the image regions and the strengths of the corresponding uncertainty indicators.

3. The method of claim 2 wherein the value of the objective function for a candidate region is based at least in part on the proximity of the candidate region to each of the image regions scaled according to the strength of the corresponding uncertainty indicator.

4. A computer-implemented method for improving an initial segmentation of 3D digital image data to obtain an updated segmentation of the 3D digital image data, the method comprising:
  obtaining an initial segmentation of the 3D digital image data;
  storing the initial segmentation of the 3D digital image data in memory accessible to a computer;
  for each of a plurality of image regions within the 3D digital image data, associating an uncertainty indicator for the initial image segmentation with the image region and assigning, by the computer, a strength to the uncertainty indicator;
  identifying, by the computer, a low-confidence region in the 3D digital image data based at least in part on proximity of the low-confidence region to the image regions and strengths of the corresponding uncertainty indicators;
  obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
  updating, by the computer, the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
  storing the updated segmentation of the 3D digital image data in the memory accessible to the computer;
  wherein identifying, by the computer, the low-confidence region in the 3D image data comprises computing, for each of a plurality of candidate regions, a value of an objective function based at least in part on proximity of the candidate region to the image regions and the strengths of the corresponding uncertainty indicators; and
  wherein the value of the objective function for a candidate region having position R is proportional to a value of an expression $$\sum_{i \in UI} s_i L(p_i, R)$$

or a mathematical equivalent thereto, where:
  UI represents a set comprising the plurality of uncertainty indicators for the initial image segmentation corresponding to the plurality of image regions and indexed by an index variable i;
  $s_i$ is the strength of the $i^{th}$ uncertainty indicator;
  $p_i$ is a position of the $i^{th}$ image region; and
  L is a proximity metric function whose value monotonically decreases with separation between R and $p_i$.

5. The method of claim 2 comprising, for each of the plurality of uncertainty indicators, assigning, by the computer, a corresponding unit normal vector to the uncertainty indicator; and wherein identifying, by the computer, the low-confidence region in the 3D digital image data is based at least in part on 3D coordinates of the unit normal vectors.

6. A computer-implemented method for improving an initial segmentation of 3D digital image data to obtain an updated segmentation of the 3D digital image data, the method comprising:
  obtaining an initial segmentation of the 3D digital image data;
  storing the initial segmentation of the 3D digital image data in memory accessible to a computer;
  for each of a plurality of image regions within the 3D digital image data, associating an uncertainty indicator for the initial image segmentation with the image region and assigning, by the computer, a strength to the uncertainty indicator;
  identifying, by the computer, a low-confidence region in the 3D digital image data based at least in part on proximity of the low-confidence region to the image regions and strengths of the corresponding uncertainty indicators;
  obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
  updating, by the computer, the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
  storing the updated segmentation of the 3D digital image data in the memory accessible to the computer;
  wherein identifying, by the computer, the low-confidence region in the 3D digital image data comprises computing, for each of a plurality of candidate regions, a value of an objective function based at least in part on proximity of the candidate region to the image regions and the strengths of the corresponding uncertainty indicators;
  wherein the method further comprises, for each of the plurality of uncertainty indicators, assigning, by the computer, a corresponding unit normal vector to the uncertainty indicator;
  wherein the value of the objective function for a planar candidate region P is proportional to a value of an expression $$\sum_{i \in UI} s_i [q_P(i) + (1 - q_P(i))L(d(p_i, P))]$$

or a mathematical equivalent thereto, where:
  UI represents a set comprising the plurality of uncertainty indicators for the initial image segmentation corresponding to the plurality of image regions and indexed by an index variable i;
  $s_i$ is the strength of the $i^{th}$ uncertainty indicator;
  $p_i$ is a position of the $i^{th}$ image region;

$q_P(i)$ is equal to $(n_i \cdot n_P)^2$, where $n_P$ represents a unit normal vector to the planar candidate region P, $n_i$ represents the unit normal vector of the $i^{th}$ uncertainty indicator and $n_i \cdot n_P$ is a dot product of $n_i$ and $n_P$;

$d(p_i,P)$ represents a distance metric proportional to a distance between the position $p_i$ of the $i^{th}$ image region and the planar candidate region P; and L represents a logistic shaped function mapping $[0,\infty) \to [0,1)$.

7. The method of claim 6 wherein $d(p,P)=|p \cdot n_P - d_P|$, where $d_P$ is an offset of the candidate region P from an origin of the 3D image data and $p \cdot n_P$ is a dot product of p and $n_P$.

8. The method of claim 2 wherein identifying, by the computer, the low-confidence region in the 3D image data comprises determining, by the computer, an extremum of the objective function with respect to the plurality of candidate regions.

9. The method of claim 2 wherein identifying, by the computer, the low-confidence region in the 3D image data comprises performing, by the computer, an optimization routine based on the computed values of the objective function.

10. The method of claim 1 wherein identifying, by the computer, the low-confidence region in the 3D image data comprises identifying, by the computer, a plurality of low-confidence regions.

11. The method of claim 10 wherein identifying, by the computer, the plurality of low-confidence regions comprises:
performing, by the computer, a first optimization routine over a set of candidate regions to identify a first low-confidence region;
re-assigning, by the computer, lower strengths to uncertainty indicators whose associated image regions are located in a vicinity of the first low-confidence region; and
performing, by the computer, a subsequent optimization routine with the re-assigned uncertainty indicator strengths to identify a subsequent low-confidence region.

12. The method of claim 11 wherein re-assigning, by the computer, lower strengths to uncertainty indicators whose associated image regions are located in the vicinity of the first low-confidence region is based on at least one user-configurable parameter indicative of a range of the vicinity of the first low-confidence region relative to the first low-confidence region.

13. The method of claim 10 comprising displaying a ranking of the plurality of low-confidence regions.

14. The method of claim 1 wherein obtaining segmentation information pertaining to the low-confidence region comprises obtaining a segmentation of the low-confidence region.

15. The method of claim 14 wherein obtaining the segmentation for the low-confidence region comprises generating, by the computer, the segmentation for the low-confidence region based at least in part on user input.

16. The method of claim 14 wherein obtaining the image segmentation for the low-confidence region comprises:
displaying image data corresponding to the low-confidence region to a user; and
obtaining a segmentation of the displayed image data based at least in part on input provided by the user.

17. A computer-implemented system for improving an initial segmentation of 3D digital image data to obtain an updated segmentation of the 3D digital image data, the system comprising a controller configured to:
obtain an initial segmentation of a 3D digital image comprising corresponding 3D image data;
store the initial segmentation of the 3D digital image data in memory accessible to the controller;
for each of a plurality of image regions within the 3D digital image data, associate an uncertainty indicator for the initial image segmentation with the image region and assign a strength to the uncertainty indicator;
identify a low-confidence region in the 3D digital image data based at least in part on proximity of the low-confidence region to the image regions and strengths of the corresponding uncertainty indicators;
obtain segmentation information pertaining to the low-confidence region and store the segmentation information pertaining to the low-confidence region in the memory accessible to the controller, wherein the segmentation information pertaining to the low-confidence region is based at least in part on user input as to a segmentation of the low-confidence region;
update the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
store the updated segmentation of the 3D digital image data in the memory accessible to the controller.

18. The method of claim 1 comprising:
for each of a plurality of subsequent image regions, associating, by the computer, a subsequent uncertainty indicator for the updated image segmentation with the subsequent image region and assigning, by the computer, a strength to the subsequent uncertainty indicator; and
identifying, by the computer, a subsequent low-confidence region in the 3D image data based at least in part on proximity of the low-confidence region to the subsequent image regions and strengths of the corresponding subsequent uncertainty indicators.

19. The method of claim 1 wherein the low-confidence region comprises a 2D surface.

20. The method of claim 19 wherein the 2D surface comprises a 2D plane.

21. The method of claim 19 wherein the 2D surface is non-planar.

22. The method of claim 1 wherein assigning, by the computer, the strength to the uncertainty indicator is based at least in part on the initial image segmentation.

23. The method of claim 1 wherein assigning, by the computer, the strength to the uncertainty indicator is based at least in part on the 3D image data.

24. The method of claim 1 wherein assigning, by the computer, the strength to the uncertainty indicator is based at least in part on trusted segmentation information.

25. The method of claim 24 wherein the trusted segmentation information comprises segmentation information provided or approved by a user.

26. The method of claim 24 wherein the trusted segmentation information comprises image segmentation information used to generate the initial image segmentation.

27. The method of claim 1 wherein assigning, by the computer, the strength to the uncertainty indicator comprises determining, by the computer, the strength based at least in part on conformance of the initial image segmentation to the 3D image data.

28. The method of claim 1 wherein assigning, by the computer, the strength to the uncertainty indicator comprises determining, by the computer, the strength based at least in part on conformance of the initial image segmentation to another image segmentation for the 3D image data.

29. The method of claim 1 wherein assigning, by the computer, the strength to the uncertainty indicator comprises determining, by the computer, the strength based at least in part on quality of the 3D image data.

30. The method of claim 1 wherein assigning, by the computer, the strength to the uncertainty indicator comprises determining, by the computer, the strength based at least in part on conformance of the initial image segmentation to one or more expected image segmentation properties.

31. The method of claim 1 wherein assigning, by the computer, the strength to the uncertainty indicator comprises determining, by the computer, the strength based at least in part on a model of efficacy of trusted segmentation information from which the initial image segmentation was determined.

32. A computer-implemented method claim 1 for improving an initial segmentation of 3D digital image data to obtain an updated segmentation of the 3D digital image data, the method comprising:
   obtaining an initial segmentation of the 3D digital image data;
   storing the initial segmentation of the 3D digital image data in memory accessible to a computer;
   for each of a plurality of image regions within the 3D digital image data, associating an uncertainty indicator for the initial image segmentation with the image region and assigning, by the computer, a strength to the uncertainty indicator;
   identifying, by the computer, a low-confidence region in the 3D digital image data based at least in part on proximity of the low-confidence region to the image regions and strengths of the corresponding uncertainty indicators;
   obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
   updating, by the computer, the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
   storing the updated segmentation of the 3D digital image data in the memory accessible to the computer;
   wherein the plurality of image regions comprises each coordinate x in a set X of coordinates that spans the 3D image data and wherein assigning the strength to the uncertainty indicator comprises, for each coordinate x in the set X of coordinates that spans the 3D image data, assigning values of a scalar uncertainty field to be the strength of the uncertainty indicator for the corresponding coordinate x.

33. The method of claim 32 wherein the scalar uncertainty field is determined in accordance with a formula of the form:

$$U(x) = \lambda_A U_A(x) + \lambda_B U_B(X) + \lambda_C U_C(x) + \ldots$$

or a mathematical equivalent there to where:
   $U_A(x), U_B(x), U_C(x), \ldots$ represent uncertainty model functions which model uncertainty contributions at the coordinate x based on different properties of one or any combination of: the initial image segmentation, the 3D image segmentation and trusted segmentation information; and
   $\lambda_A, \lambda_B, \lambda_C, \ldots$ represent weighting factors for the respective uncertainty model functions $U_A(x), U_B(x), U_C(x), \ldots$.

34. The method of claim 33 wherein identifying, by the computer, the low-confidence region in the 3D digital image data comprises identifying a planar low-confidence region according to $$\mathrm{argmax}_P(\iint_P U(x) dA)$$

where:
   U(x) represents the uncertainty field at the coordinate x; and
   P is a candidate plane,
with the condition that U(x) is limited to the set X of coordinates that spans the 3D image data and zero-valued elsewhere.

35. A computer-implemented method for improving an initial segmentation of 3D digital image data to obtain an updated segmentation of the 3D digital image data, the method comprising:
   obtaining an initial segmentation of the 3D digital image data;
   storing the initial segmentation of the 3D digital image data in memory accessible to a computer;
   for each of a plurality of image regions within the 3D digital image data, associating an uncertainty indicator for the initial image segmentation with the image region and assigning, by the computer, a strength to the uncertainty indicator;
   identifying, by the computer, a low-confidence region in the 3D digital image data based at least in part on proximity of the low-confidence region to the image regions and strengths of the corresponding uncertainty indicators;
   obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
   updating, by the computer, the initial segmentation of the 3D digital image data to obtain an updated segmentation of the 3D digital image data, wherein updating the initial segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the initial segmentation of the 3D digital image data; and
   storing the updated segmentation of the 3D digital image data in the memory accessible to the computer;

wherein obtaining the initial segmentation of the 3D image data comprises:
obtaining at least one 2D image segmentation for the 3D image data;
placing seeds in an unvisited plane at intersections of the at least one 2D image segmentation with the unvisited plane;
ordering the seeds in the unvisited plane; and
obtaining an automatic 2D image segmentation of the unvisited plane based on the ordered seeds.

36. The method of claim 35 wherein the low-confidence region comprises a 2D image region and comprising:
obtaining a 2D image segmentation for the low-confidence region;
placing additional seeds in the unvisited plane at intersections of the 2D image segmentation for the low-confidence region with the unvisited plane;
ordering the seeds and additional seeds in the unvisited plane; and
obtaining an automatic 2D image segmentation of the unvisited plane based on the ordered seeds and additional seeds.

37. The method of claim 36 wherein obtaining the 2D image segmentation for the low-confidence region comprises obtaining the 2D image segmentation for the low-confidence region using a 2D Livewire algorithm.

38. A computer-implemented method for improving a first segmentation of 3D digital image data to obtain an updated segmentation of the 3D digital image data, the method comprising:
obtaining a 3D digital image comprising corresponding 3D image data and a first segmentation of the 3D image data;
storing the first segmentation of the 3D digital image data in a memory accessible to the computer
for each of a plurality of image regions within the 3D digital image data, associating an uncertainty indicator for the first image segmentation with the image region and assigning, by the computer, a strength to the uncertainty indicator;

identifying, by the computer, a low-confidence region in the 3D digital image data based at least in part on proximity of the low-confidence region to the image regions and strengths of the corresponding uncertainty indicators; and
recommending the low-confidence region by outputting the low-confidence region to thereby indicate that the low-confidence region comprises the image region for which further user input would be desirable;
obtaining segmentation information pertaining to the low-confidence region and storing the segmentation information pertaining to the low-confidence region in the memory accessible to the computer, wherein the segmentation information pertaining to the low-confidence region is based at least in part on user input as to a segmentation of the low-confidence region;
updating, by the computer, the first segmentation of the 3D digital image data to obtain an updated segmentation of the 3D digital image data, wherein updating the first segmentation of the 3D digital image data to obtain the updated segmentation of the 3D digital image data is based on the segmentation information pertaining to the low-confidence region and thereby benefits from the user input to achieve improved accuracy of the updated segmentation of the 3D digital image data relative to the first segmentation of the 3D digital image data; and
storing the updated segmentation of the 3D digital image data in the memory accessible to the computer.

39. A computer program product for segmenting 3D image data, the program product comprising a non-transitory computer-readable medium having executable code configured to cause a processor executing the code to perform the method of claim 1 for segmenting 3D image data.

40. A computer program product for segmenting 3D image data, the program product comprising a non-transitory computer-readable medium having executable code configured to cause a processor executing the code to perform the method of claim 38.

* * * * *